(12) United States Patent
Shaughnessy et al.

(10) Patent No.: US 7,741,035 B2
(45) Date of Patent: *Jun. 22, 2010

(54) USE OF GENE EXPRESSION PROFILING TO PREDICT SURVIVAL IN CANCER PATIENT

(75) Inventors: John D. Shaughnessy, Little Rock, AR (US); Bart Barlogie, Little Rock, AR (US); Fenghuang Zhan, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 950 days.

This patent is subject to a terminal disclaimer.

(21) Appl. No.: 11/147,829

(22) Filed: Jun. 8, 2005

(65) Prior Publication Data

US 2006/0003365 A1 Jan. 5, 2006

Related U.S. Application Data

(63) Continuation-in-part of application No. 11/133,937, filed on May 20, 2005.

(60) Provisional application No. 60/606,319, filed on Sep. 1, 2004, provisional application No. 60/573,669, filed on May 21, 2004.

(51) Int. Cl.
*C12Q 1/68* (2006.01)
*G01N 33/48* (2006.01)

(52) U.S. Cl. .............................. 435/6; 436/64
(58) Field of Classification Search ................ None
See application file for complete search history.

(56) References Cited

U.S. PATENT DOCUMENTS

2005/0164231 A1* 7/2005 Staudt et al. ................ 435/6

OTHER PUBLICATIONS

Zhan et al., Global gene expression profiling of multiple myeloma, monoclonal gammopathy of undertermined significance, and normal bone marrow plasma cells, Mar. 2002, Blood, vol. 99, pp. 1745-1757.*
Cole et al., The genetics of cancer—a 3D model, Jan. 1999, Nature, vol. 21, pp. 38-41.*
Lockhart et al., Genomics, gene expression and DNA arrays, Jun. 2000, Nature, vol. 405, pp. 827-836.*

* cited by examiner

*Primary Examiner*—Marjorie Moran
*Assistant Examiner*—Jason M Sims
(74) *Attorney, Agent, or Firm*—Benjamin Aaron Adler

(57) ABSTRACT

Gene expression profiling in multiple myeloma patients identifies genes that distinguish between patients with subsequent early death or long survival after treatment. Poor survival is linked to over-expression of genes such as ASPM, OPN3 and CKS1B which are located in chromosome 1q. Given the frequent amplification of 1q in many cancers, it is possible that these genes can be used as powerful prognostic markers and therapeutic targets for multiple myeloma and other cancer.

4 Claims, 13 Drawing Sheets

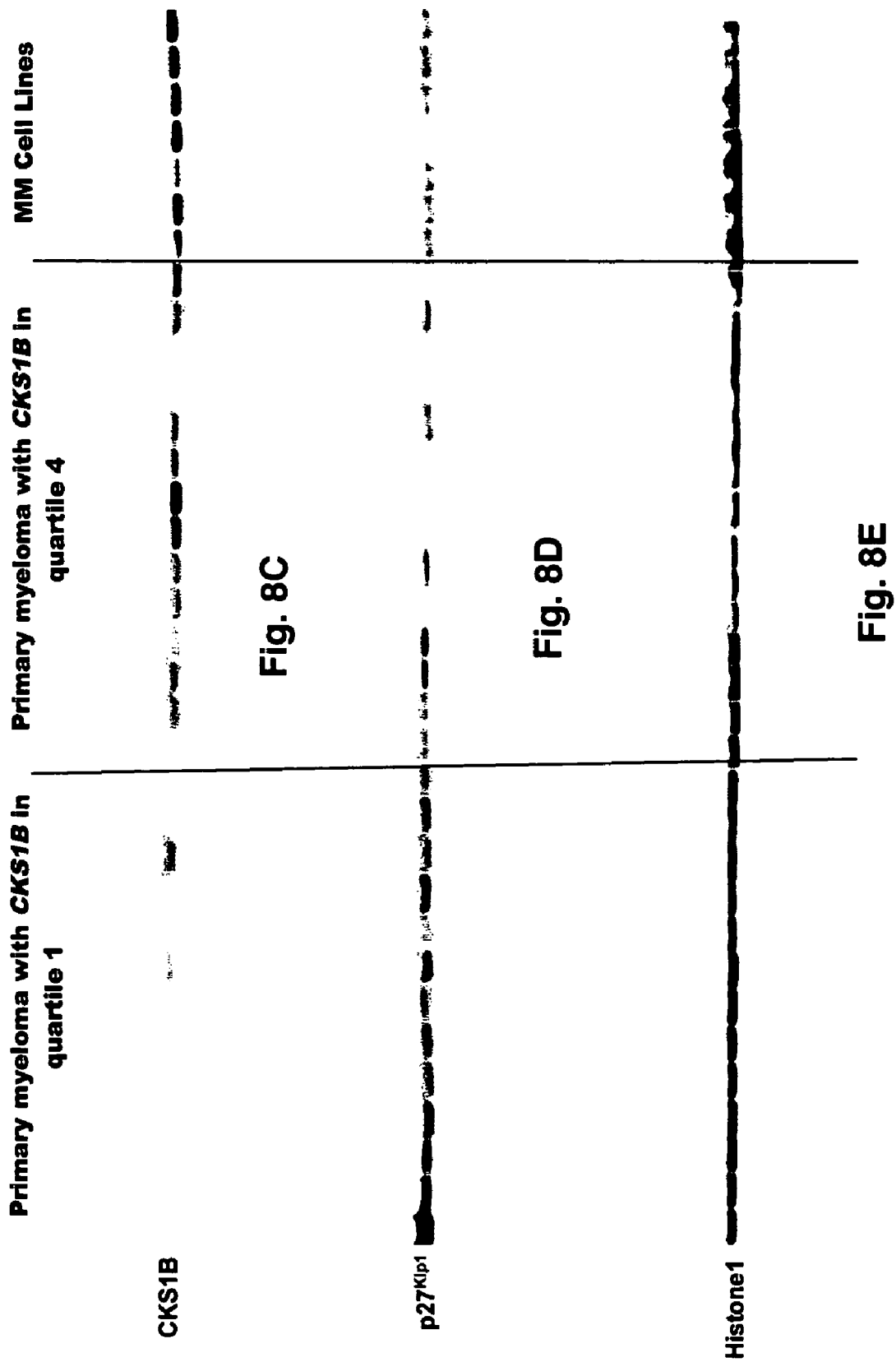

SEQUENCE LISTING

```
<160> NUMBER OF SEQ ID NOS: 1

<210> SEQ ID NO 1
<211> LENGTH: 60
<212> TYPE: DNA
<213> ORGANISM: artificial sequence
<220> FEATURE:
<223> OTHER INFORMATION: a synthetic oligonucleotide sequence
      corresponding to CKS1B.

<400> SEQUENCE: 1
gatccccgga catagccaag ctggtcttca agagagacca gcttggctat           50
gtccttttta                                                       60
```

USE OF GENE EXPRESSION PROFILING TO PREDICT SURVIVAL IN CANCER PATIENT

CROSS-REFERENCE TO RELATED APPLICATIONS

This is a continuation-in-part of non-provisional application U.S. Ser. No. 11/133,937, filed May 20, 2005, which claims benefit of provisional patent applications U.S. Ser. No. 60/606,319, filed Sep. 1, 2004 and U.S. Ser. No. 60/573,669, filed May 21, 2004, both now abandoned.

FEDERAL FUNDING LEGEND

This invention was produced in part using funds obtained through a grant R33 CA97513-01 from the National Cancer Institute. Consequently, the federal government has certain rights in this invention.

BACKGROUND OF THE INVENTION

1. Field of the Invention

The present invention relates generally to the field of cancer research. More specifically, the present invention relates to gene expression profiling in cancer patients.

2. Description of the Related Art

A frustrating aspect of cancer chemotherapy is the unpredictable variability of induction or duration of response and long-term survival. A significant number of patients (approximately 20%) derive no tangible benefit from the therapy, but still are subjected to drug toxicity, secondary risk, reduced quality of life, and delay in treatment that might have been effective.

Multiple myeloma is an invariantly fatal B cell malignancy that manifests at the plasma cell stage of differentiation. Although multiple myeloma initially resides in the bone marrow, it can transform into an aggressive disease with increased proliferation (resulting in a higher frequency of abnormal metaphase karyotypes), elevated LDH and extramedullary manifestations (Barlogie B. et al., 2001). Additionally, the clinical course of multiple myeloma and its response to therapy is influenced by special molecular genetic lesions and tumor cell-microenvironment interaction (Kuehl et al., 2002; Shaughnessy et al., 2003; Hideshima, et al., 2004; Fonseca et al., 2004). Although complete response can be obtained in more than 40% of patients with high-dose therapy, survival can vary from few months to more than fifteen years (Attal et al., 2003; Barlogie et al., 2004). Furthermore, high-risk disease is best captured by abnormal metaphase cytogenetics, present in 30% to 50% (DeWald et al., 1985; Smadja et al., 2001; Shaughnessy et al., 2003) of newly diagnosed patients and reflecting a higher proliferative capacity and stromal cell-independence of the malignant clone. However, karyotypes of multiple myeloma are notoriously complex and have until recently defied cytogenetic classification. Nevertheless, a comprehensive correlative analyses of multiple myeloma karyotypes with patient survival from multiple laboratories now reveal that hyperdiploid, non-hyperdiploid, chromosome 13 deletion-positive, t(4;14)(p16;q32)-positive, and t(11;14)(q13;q32)-positive forms of the disease likely represent unique subclasses with divergent clinical outcomes.

While the presence of an abnormal karyotype has emerged as the single most significant prognostic variable in predicting outcome in patients receiving high dose chemotherapy and tandem stem cell transplants, this variable in combination with other historically relevant clinical parameters, e.g. serum albumin, b2M, and lactate dehydrogenase, account for no more than 30% of the variability in outcome in this disease. Thus, there is a need for more robust risk stratification algorithms for this disease.

Multiple myeloma is characterized by complex karyotypes and chromosome 1 instability at the cytogenetic level. Chromosome 1 instability generally involves partial duplications, whole-arm translocations or jumping translocations of 1q identified by G-banding. This instability was further characterized recently using a combination of spectral karyotyping and fluorescence in situ hybridization (FISH) with probes for satII/III (1q12), BCL9 (1q21), and IL6R (1q21) on the karyotypes of 44 patients with known 1q aberrations (Sawyer et al., 2004). In eight patients segmental duplication of 1q12-21 and adjacent bands occurred on non-homologous chromosomes. In five cases, the 1q first jumped to a non-homologous chromosome, after which the 1q12-21 segment subsequently again duplicated itself one to three times. In three other cases, segmental duplications occurred after the 1q first jumped to a non-homologous chromosome and then duplicated the adjacent proximal non-homologous chromosome segment prior to jumping or inserting to a new location. These cases demonstrate that satII/III DNA sequences are not only associated with duplication of adjacent distal chromosome segments after translocation, but are also associated with duplication and jumping/insertion of proximal non-homologous chromosome segments (Sawyer et al., 2004).

In B-acute lymphoblastic leukemia and many other advanced neoplasia, extra copies of 1q may confer a proliferative advantage on the tumor cells. Currently, the ultimate molecular target(s) of the 1q21 amplification and jumping in 1q in myeloma and many other cancers is not known. The prior art is thus deficient in providing a chromosome 1 marker(s) or a chromosome 13 marker(s) useful for initial staging as well as disease follow-up for multiple myeloma and other types of cancer. The present invention fulfills this long-standing need and desire in the art.

SUMMARY OF THE INVENTION

Global gene expression profiling has emerged as powerful tool for classifying disease subtypes and developing robust prognostic models in leukemia and lymphoma (Shipp et al., 2002; Yeoh et al., 2002; Rosenwald et al., 2002; Bullinger et al., 2004; Valk et al., 2004). Microarray studies in myeloma have also provided key insights into its biology and clinical behavior (Zhan et al., 2002; De Vos et al., 2002; Claudio et al., 2003; Tian et al., 2003).

In the present invention, gene expression profiles of malignant plasma cells were examined in an effort to identify the molecular signatures of early treatment failure after high dose chemotherapy and autologous peripheral blood stem cell transplantation. Results disclosed herein reveal a clear gene expression signature that portends for a highly aggressive form of multiple myeloma. Markers identified herein are useful for initial staging and disease follow-up for prediction of relapse of multiple myeloma and other types of cancer. Moreover, these predictive genes, their protein products and the biological pathways in which they function represent potential points of therapeutic intervention for multiple myeloma and other types of cancer.

The present invention provides a method of determining the prognosis of a multiple myeloma patient based on reduced expression, overexpression or their combination of one or more genes discussed herein.

The present invention also provides a method of determining the prognosis of a multiple myeloma patient based in decreased copy number, increased copy number or their combinations of one or more genes discussed herein. The present invention further provides a method of determining the risk of developing a disease-related event for a cancer patient based on overexpression of one or more of the genes identified herein as being overexpressed. The present invention still further provides a method of using agents that downregulate the expression of CKS1B gene or CKS1B gene product to treat a cancer patient having overexpression of CKS1B. The present invention also provides a method of using compounds that downregulate the expression of CKS1B gene or CKS1B gene product and a vector comprising DNA sequence encoding RFP2 gene to treat an individual having high-risk multiple myeloma.

The present invention further provides a kit comprising (a) probe specific for CKS1B gene, (b) probe specific for RFP2 gene or their combinations.

In addition, the present invention provides uses of 1q as prognostic and therapeutic targets in many cancers, including as a diagnostic, prognostic, or therapeutic target in myeloma. A person having ordinary skill in this art would be able to detect aggressive disease by detecting CKS1B, OPN3, and ASPM alone or in combination by DNA copy using, but not limited to DNA arrays, interphase or metaphase FISH. Measuring gene expression levels by microarray or RT-PCR or the like, or measuring protein by tissue array, flow cytometry, immunohistochemistry or any other method of measuring protein content in tumor cells would be valuable predictors of patient survival from various types of cancers. Since 1q amplification is a progressive event, continually testing for amplification of these genes during the disease management could identify the onset of aggressive behavior. Finally, since the CKS1B is a small molecule with a powerful role in biology it represents a potential therapeutic target. A person having ordinary skill in this art would be able to manipulate this genes' copy number, its message through RNA1, antibody and or small molecule interference as a means of therapy.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

FIG. 5A shows box plots of log base 2-transformed Affymetrix signal (y-axis) among 351 cases according to quartile expression levels (x-axis). FIG. 5B shows Kaplan-Meier plots of overall survival reveal inferior outcome among the 88 patients with $4^{th}$ quartile expression levels of CKS1B compared to the remaining 263 patients with quartile 1-3 expression levels.

FIG. 6A shows metaphase fluorescence in situ hybridization analysis of CKS1B at 1q21 (red signal) and ASPM at 1q31 (green signal) performed on plasma cells from a patient with myeloma. Note the arrows pointing to tandem duplications of CKS1B and their higher prevalence relative to 1q31. FIG. 6B shows box plots of log base 2-transformed Affymetrix Signal (y-axis) by CKS1B amplification (N=197). In box plots, the top, bottom, and middle lines corresponded to the $75^{th}$, $25^{th}$ and $50^{th}$ percentiles, respectively, and the whiskers extended to the nearest point not beyond 1.5 times the inter-quartile range, with observations beyond these indicated by individual lines. A Wilcoxon rank sum test was used to compare Signal across copy number categories. FIG. 6C shows a Kaplan-Meier plot of overall survival in the validation cohort depicts inferior outcomes among the 89 patients with CKS1B amplification compared to the remaining 135, as determined by interphase fluorescence in situ hybridization. FIG. 6D shows the Kaplan-Meier plot, as in 6C, for the combined sample of 421 patients.

FIGS. 8A-E show that CKS1B mRNA correlates with nuclear protein levels and inversely correlates with CDKN1B and siRNA to CKS1B and can reduce cell proliferation in myeloma cell lines. FIG. 8A shows CKS1B and FIG. 8B shows CDKN1B (CDKN1B) gene expression signal in 1000 unit increments is plotted on the y-axis. Primary myelomas with CKS1B expression in quartile 1 (n=13) and quartile 4 (n=14) and myeloma cell lines (n=7) were grouped and plotted from left to right along the x-axis. Each bar represented a sample and the height indicated the level of gene expression in the sample. Western blot analysis of nuclear protein extracts for CKS1B (FIG. 8C), phospho-thr-187-CDKN1B (FIG. 8D), and Histone 1A (loading control; FIG. 8E) from aliquots of same plasma cells used in 8A and 8B. Samples were ordered from left to right in the exact same order in all panels.

DETAILED DESCRIPTION OF THE INVENTION

Figure 1A:
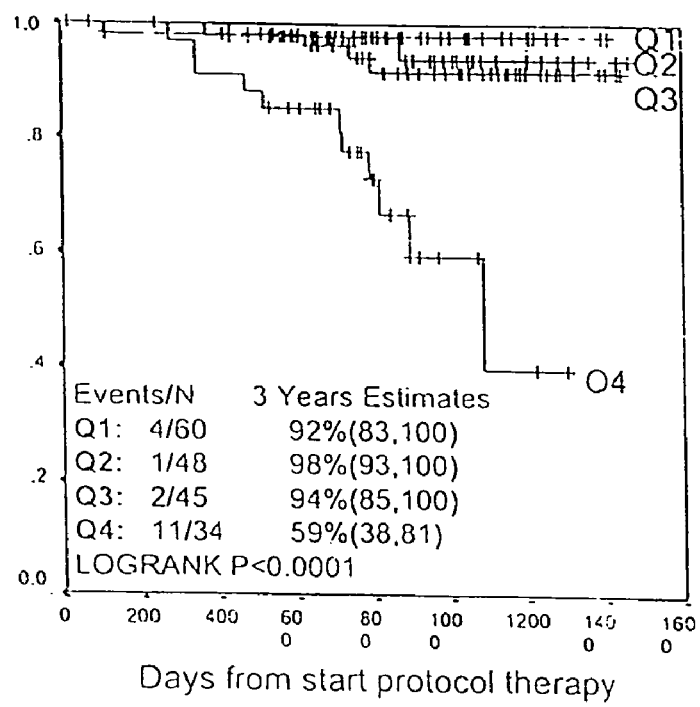
FIGS. 1A-B show Kaplan Meier survival curve analysis of event-free survival (FIG. 1B) and overall survival (FIG. 1A) in relation to CKS1B expression levels. The patient samples were grouped into quartiles based on levels of gene expression. Q1 was the lowest quartile and Q4 was the highest. Note the significant link between Q4 and poor prognosis.

The variability in survival among patients with myeloma can range from months to more than 15 years. Patients at highest risk are best identified by the presence or absence of an abnormal karyotype. However, this test only accounts for ~15% of the variability in outcome. Thus, many patients who present with no cytogenetic abnormalities experience rapid relapse and/or early death. To better define high-risk disease and also potentially identify genetic mechanisms that give rise to this poor survival, gene expression patterns were analyzed in freshly isolated plasma cells from 40 newly diagnosed myeloma patients who were then treated with tandem stem cell transplants. Patients were separated into two groups of 20 each. Those in the "short-survival" group all died within 900 days of initiation of therapy. Patients in the "long-survival" group survived more than 1,453 days. RNA from plasma cells was labeled and hybridized to the U133Plus2.0 microarrays. The expression value was transformed by log base 2 and each sample was normalized to give a mean of 0 and a variance of 1. Chi-square analyses and t-tests were used to identify genes whose expression patterns were unique to each group.

A total of 1770 probe sets were significantly differentially expressed between the two groups (P<0.05). A total of 1,025 (58%) of the probe sets were elevated in the short-survival group. An overwhelming majority, 290 of the 1,770 genes (19%), mapped to chromosome 1. Of the 1,770 probe sets, 84 demonstrating a >2-fold difference in expression were further analyzed with Kaplan-Meier survival analyses. In this test, 17 genes were highly significant (P<0.0001) (Table 1). Of the 17 genes identified, 10 (59%) map to chromosome 1. Of these 10 genes, all 4 genes from the p arm were down-regulated while all 6 genes from the q arm were up-regulated in the short-survival group.

Figure 1B:
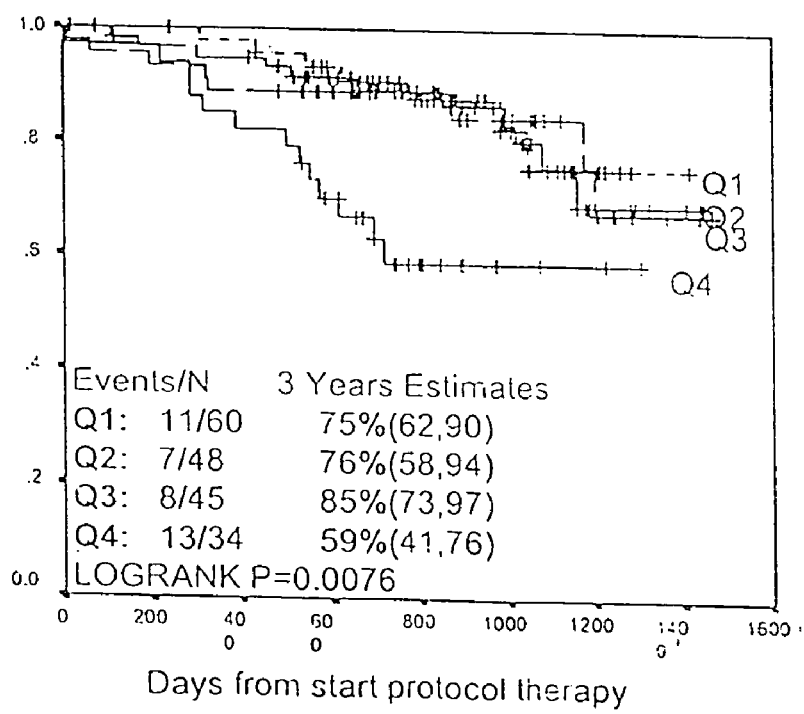

It has been previously demonstrated that jumping 1q and amplification of genes from 1q21 represent common genetic lesions in myeloma. Fluorescence in situ hybridization analysis of BCL9 and IL-6R has shown that these genes can define a 1q21 amplicon. However, BCL9 and IL-6R were not linked to disease outcome. The present invention found that CKS1B, which is located very near the 1q21 amplicon, is over-expressed in myelomas and highly correlated with overall survival (FIG. 1A) and event-free survival (FIG. 1B). CKS1B is an evolutionarily conserved protein that interacts genetically and physically with cyclin-dependent kinases and promotes mitosis. Quantitative RT-PCR was used to confirm the microarray results for this gene. Given the important role of CKS1B in controlling mitosis, CKS1B over-expression, possibly as a result of gene amplification, may impart a highly aggressive phenotype on malignant plasma cells.

Using microarray correlative studies with 350 newly diagnosed cases with overall survival longer or less than 2 years from start of therapy, it was found that elevated expression of genes from chromosome 1q was a glaring feature of early death. Using statistical modeling, a three gene model is disclosed herein that could capture >80% of all early deaths. These three genes all mapped to chromosome 1. The genes from 1q telomere to centromere are: OPN3 (1q43), ASPM (1q31.3) and CKS1B (1q21). The CKS1B chromosome map position, only 200 Kb telomeric of IL6R, suggests that this gene is the target of 1q21 amplification in myeloma. Moreover, given the frequent amplification of 1q in many cancers, it is possible that CKS1B, alone or together with the other two genes identified above, may be a ubiquitous marker/target for cancer in general.

CKS1B and Cell Cycle Control

CKS1B was originally defined by their ability to bind CDK/cyclin complexes. CKS1B is a highly conserved protein of 79 amino acids that has two homologs in higher eukaryotes. The human orthologs can functionally substitute for CKS1 in yeast. Most genetic and biochemical data point to a mitotic role for CKS proteins. Loss of function of CKS1 results in M phase arrest with condensed but unsegregated chromosomes, an extended spindle and elevated levels of Cdc2/cyclin B kinase activity. CKS1 also has a G1 function. Immunodepletion of CKS1 ortholog Xep9 from interphase egg extracts prevented entry into mitosis, whereas depletion from mitotic exacts leads to M phase arrest with elevated levels of cyclin B and CDK1/cyclin B kinase activity. These data suggests that CKS proteins may be required for both entry into and progression through mitosis.

DNA synthesis is mediated by the action of the cyclin E/CDK2 complex, which is in turn negatively regulated by the cyclin-dependent kinase inhibitor CDKN1B (Sherr and Roberts, 1999). The small evolutionarily conserved protein CKS1 is required for SCF$^{Skp2}$-mediated ubiquitinylation and proteasomal degradation of cyclin-dependent kinase inhibitor CDKN1B (Ganoth et al., 2001; Spruck et al., 2001). CDKN1B degradation not only permits DNA replication but also ensures the correct progression of cells through S phase into mitosis (Nakayama et al., 2004) and Cks proteins interact with the proteasome to control the proteolysis of mitotic cyclins by way of regulating the transcriptional activity of CDC20 (Morris et al., 2003), a regulatory subunit of the anaphase-promoting complex/cyclosome ubiquitin ligase (Peters, 2002). Thus, CKS1 and the SCF$^{Skp2}$-CDKN1B-Cdk1/2 axis appear to be important for both DNA synthesis and mitosis (Pagano, 2004). The low CDKN1B protein levels in cancer cells, in the absence of gene mutations, has prompted speculation that hyper-activation of CKS1B and/or SKP2, may account for the low levels of CDKN1B (Slingerland and Pagano, 2000). Moreover, CKS1B also regulates G2 to M transition by controlling cyclin B degradation by APC.

CKS1B and Cancer

Results disclosed below identify CKS1B located at 1q21 as a strong candidate gene for conferring poor prognosis in patients getting tandem stem cell transplants for their myeloma. Fluorescence in situ hybridization analysis confirmed elevated expression of CKS1B; therefore, survival was directly related to CKS1B gene transcription activity and copy number in newly diagnosed patients. There has been a suggestion that prior therapy and long latency results in amplification event. Young (<50 years) patients are as likely to present with elevated CKS1B as old patients (>60 years). Data from 20 patients with baseline and relapse samples showed that CKS1B gene amplification and increased expression was increased in patients who had normal baseline values. These data suggest that CKS1B amplification can be present at diagnosis and linked to poor survival and can be amplified during the course of fulminate relapse.

Primary numerical chromosome aberrations seen in multiple myeloma karyotypes apparently evolve over an extended period of time as the disease remains a subclinical phenomenon (MGUS). In later stages of progressive multiple myeloma cytogenetic evolution takes place, resulting in acquisition of additional abnormalities usually involving chromosome 1. Trisomy of chromosome 1 is seen in 40% of myeloma karyotypes, and trisomy of the long arm of chromosome 1q is common in many cancers such as leukemia and lymphomas. Duplicated 1q might be a secondary mutations associated with disease progression. Trisomy of 1q has also been linked to metastatic potential of colon and renal cell carcinomas.

Given its central role in regulating cell cycle progression, its location in a frequently amplified region in human cencer and its link to myeloma cell proliferation and patient survival, CKS1B is considered as a candidate gene whose amplification and induced over-expression confers a poor prognosis in many cancers. To test this, the present invention determined CKS1B copy number in various cell lines and also determined if siRNA to CKS1B was effective in killing the other forms of cancer. This is the first report indicating that the CKS1B gene may be an oncogene and that this oncogene plays a role in acquiring drug resistance and rapid death in myeloma. The frequency of this genetic defect in myeloma and other cancers such as leukemia, lymphomas, breast cancer, colon cancer and prostate cancer suggests that CKS1B amplification is a frequent mechanism by which tumors develop highly proliferative and multi-drug resistant disease. Development of small molecule inhibitors of CKS1B may be a future therapeutic strategy, and CKS1B could be a powerful marker for initial staging and disease follow-up for prediction of imminent relapse by detecting CKS1B amplification with techniques such as gene expression profiling, fluorescence in situ hybridization or immunohistochemistry. In addition to over-expression of a gene, reduced expression of RFP2 gene on chromosome 13q14 either alone or in combination with over-expression of CKS1B gene may play a significant role in the diagnosis of multiple myeloma.

In one embodiment of the present invention, there is provided a method of determining the prognosis of a multiple myeloma patient, comprising the steps of: obtaining plasma cells from said patient, determining gene expression of one or more genes from the group consisting of GNG10, PNPLA4, KIAA1754, AHCYL1, MCLC, EV15, AD-020, PARG1, CTBS, FUCA1, RFP2, FLJ20489, LTBP1, TRIP13, AIM2, SELI, SLC19A1, LARS2, OPN3, ASPM, CCT2, UBE2I, STK6. FLJ13052, FLJ12525, BIRC5, CKS1B, CKAP1, MGC57827, DKFZp7790175, PFN1, ILF3, IFI16, TBRG4, PAPD1, EIF2C2, MGC4308, ENO1, DSG2, EXOSC4, TAGLN2, RUVBL1, ALDOA, CPSF3, MGC15606, LGALS1, RAD18, SNX5, PSMD4, RAN, KIF14, CBX3, TMPO, DKFZP586LO724, WEE1, ROBO1, TCOF1, YWHAZ, MPHOSPH1 in the plasma cell, and comparing the expression level of the gene(s) with expression level of the gene in a control individual, where reduced expression, overexpression of the gene or their combination compared to the gene expression levels in plasma cell of a control individual indicates that the patient would have a poor prognosis.

A patient having a poor prognosis is the one who is at risk of developing aggressive form of the disease, suffering from relapse or will have a shorter life expectancy. Specifically, the reduced expression of the gene, overexpression of the gene or their combination in a patient after treatment predicts risk of relapse in the patient after treatment. Examples of the treatment that such a patient would have undergone is high dose chemotherapy and autologous peripheral blood stem cell transplantation. Examples of the genes with a reduced expression although not limited to include GNG10, PNPLA4, KIAA1754, AHCYL1, MCLC, EV15, AD-020, PARG1, CTBS, FUCA1, RFP2, FLJ20489 or LTBP1. Furthermore, examples of the genes that are overexpressed although not limited to include TRIP13, AIM2, SELI, SLC19A1, LARS2, OPN3, ASPM, CCT2, UBE2I, STK6. FLJ13052, FLJ12525, BIRC5, CKS1B, CKAP1, MGC57827, DKFZp7790175, PFN1, ILF3, IFI16, TBRG4, PAPD1, EIF2C2, MGC4308, ENO1, DSG2, EXOSC4, TAGLN2, RUVBL1, ALDOA, CPSF3, MGC15606, LGALS1, RAD18, SNX5, PSMD4, RAN, KIF14, CBX3, TMPO, DKFZP586LO724, WEE1, ROBO1, TCOF1, YWHAZ or MPHOSPH1. Specifically, the gene that is overexpressed is CKS1B gene and the gene with reduced expression is the RFP2 gene. Additionally, the control individual is a normal, healthy individual or an individual diagnosed with multiple myeloma lacking overexpression of the gene, reduced expression of the gene or a combination thereof. Moreover, the gene expression may be determined by DNA microarray or RT-PCR.

In another embodiment of the present invention, there is provided a method of determining the prognosis of a multiple myeloma patient, comprising the steps of: obtaining plasma cell from the patient, and determining copy number of one or more genes discussed supra, where a decreased copy number, increased copy number or a combination thereof compared to copy number in a plasma cell of a control individual indicates that the patient would have poor prognosis. As discussed supra, a decreased copy number, increased copy number of the gene or their combination in a patient after treatment predicts risk of relapse after treatment. The type of treatment is the same as discussed supra.

Additionally, examples of the genes with decreased copy is the same as the genes with reduced expression whereas examples of the gene with increased copy number is the same as the genes with overexpression. Furthermore, a preferred gene with an increased copy number is the CKS1B gene and a preferred gene with a reduced copy number is the RFP2 gene. The control individual in this method is a normal healthy individual or an individual diagnosed with multiple myeloma lacking the decreased copy number, increased copy number of the gene or their combination. Furthermore, the copy number of the gene is determined by fluorescence in situ hybridization. In a further related embodiment of the present invention is a kit comprising; probe(s) specific for one or more of the genes discussed supra.

In a yet another embodiment of the present invention, there is provided a method of determining the risk of developing a disease-related event for a cancer patient. Such a method comprises the steps of: obtaining biological samples from the patient, and determining gene expression levels, copy number or their combination of one or more genes belonging to the group discussed above as being overexpressed, where overexpression, increased copy number of the gene or a combination thereof compared to the gene expression levels, copy number of their combination in a normal individual indicates that the patient would have an increased risk of developing a disease-related event. Representative examples of the gene that is overexpressed or has an increased copy number is OPN3, CKS1B or ASPM gene.

Generally, the disease-related event consists of death, progression to an aggressive form of the disease and relapse. Additionally, the cancer patient may be an individual with 1q21 amplification. Such an individual may be a multiple myeloma, breast cancer, colon cancer or prostate cancer patient. Moreover, the control individual is the same as in the methods described supra. Furthermore, the gene expression level or copy number is determined either before or after treatment of the patient. The type of treatment, the method used to determine the gene expression level and copy number is the same as discussed supra. Additionally, the gene expression level is determined at the protein level. Examples of such methods although not limited to include flow cytometry, immunohsitochemistry and tissue array.

In another embodiment of the present invention, there is provided a method of treating a cancer patient having overexpression of CKS1B gene or CKS1B gene product, comprising the step of administering to the patient an agent that downregulates the expression of the CKS1B gene or the CKS1B gene product. Such a patient may be an individual with 1q21 amplification. Furthermore, such an individual may be a multiple myeloma, a breast cancer, a colon cancer or a prostate cancer patient. Examples of agents that downregulate the expression of the CKS1B gene are not limited to but include RNA mediated interference or a peptide nucleic acid (PNA). The RNA mediated interference may be a small interfering RNA (siRNA) with a sequence shown in SEQ ID No. 1 or a vector comprising the small interfering RNA sequence. Representative examples of such vectors are lentiviral vector although a person having ordinary skill in this art would readily recognize that other viral vectors could be employed with routine experimentation. Examples of agents that downregulate the expression of CKS1B gene are not limited to but include anti-sense oligonucleotides, antibodies or a small molecule inhibitors that are well known to or may be readily developed by one of ordinary skill in the art.

In yet another embodiment of the present invention, there is provided a method of treating an individual having high-risk multiple myeloma, comprising administering to the individual pharmaceutically effective amounts of a compound that downregulates the expression of CKS1B gene or CKS1B gene product and a vector comprising DNA sequence encoding RFP2 gene. The examples of compounds that down regulate the expression of CKS1B gene or its product are the same as discussed supra.

In still yet another embodiment of the present invention, there is provided a kit, comprising; (a) probe specific for CKS1B gene, (b) probe specific for RFP2 gene, or their combinations.

The present examples, along with the methods, procedures, treatments, molecules, and specific compounds described herein are presently representative of preferred embodiments and are not meant to limit the present invention in any fashion. One skilled in the art will readily appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Overall Survival Linked to Gain of Chromosome 1 Genes

This example discloses gene expression profiling data identifying genes whose expression in malignant plasma cells of newly diagnosed myeloma patients is significantly correlated with early death in patients treated with tandem stem cell transplants.

Figure 2:
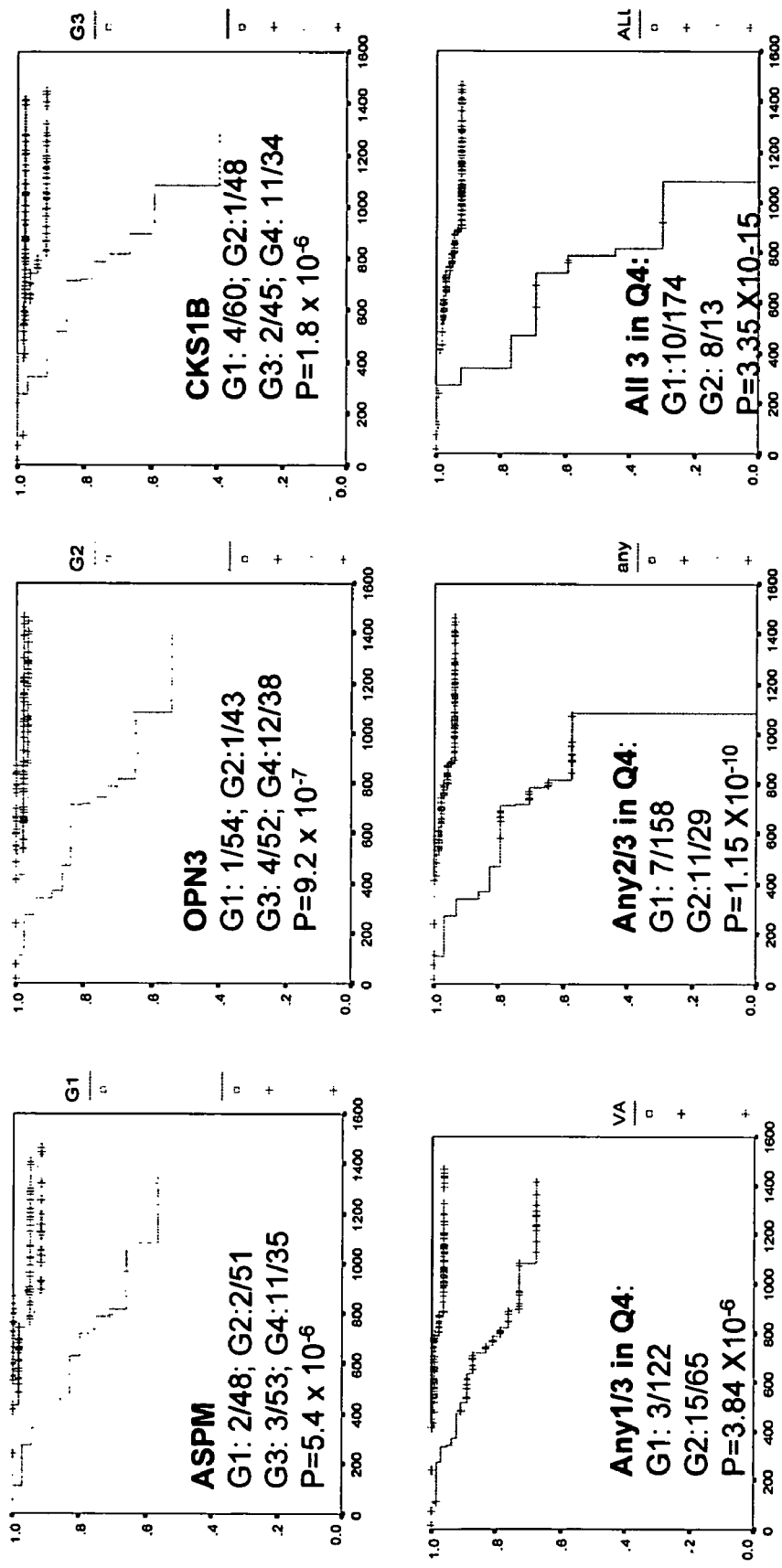
FIG. 2 shows overall survival analysis on patients with more than 1.5 years follow-up. Patient samples were grouped into quartiles based on levels of gene expression. Q1 was the lowest quartile and Q4 was the highest. Note the significant link between poor prognosis and elevated expression of ASPM, OPN3 or CSK1B (upper panel). The power of survival prediction was increased by grouping two or more of the three genes in the analysis (lower panel).

FIG. 2 shows overall survival analysis on patients with more than 1.5 years follow-up. Patient samples were grouped into quartiles based on levels of gene expression. Q1 is the lowest quartile and Q4 is the highest. There was significant link between poor prognosis and elevated expression of ASPM, OPN3 or CSK1B (FIG. 2, upper panel). The power of survival prediction was increased by grouping two or more of these three genes in the analysis (FIG. 2, lower panel).

Figure 3A:
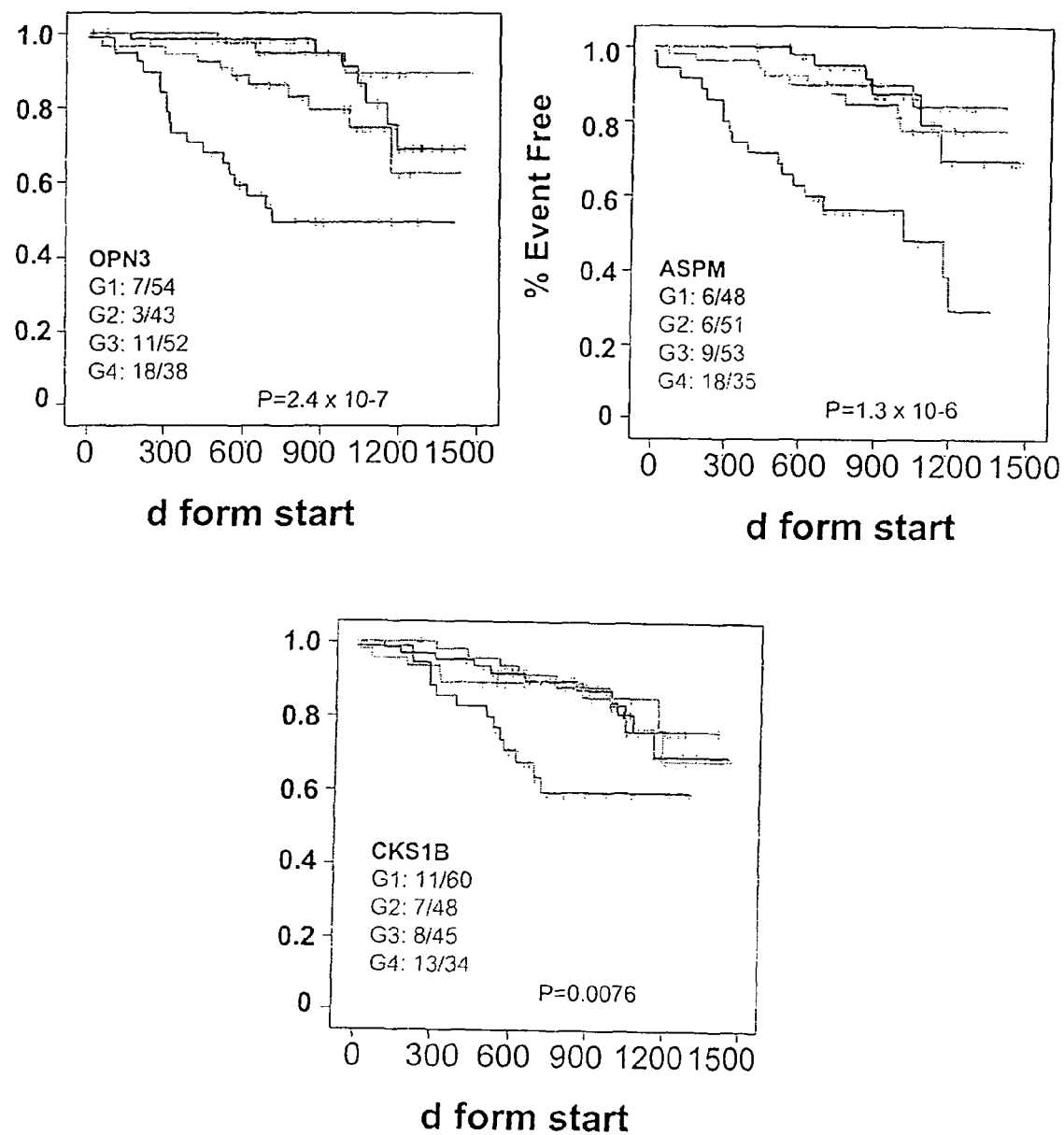
FIG. 3A shows ASPM, OPN3 or CSK1B can also predict event-free survival.
Figure 3B:
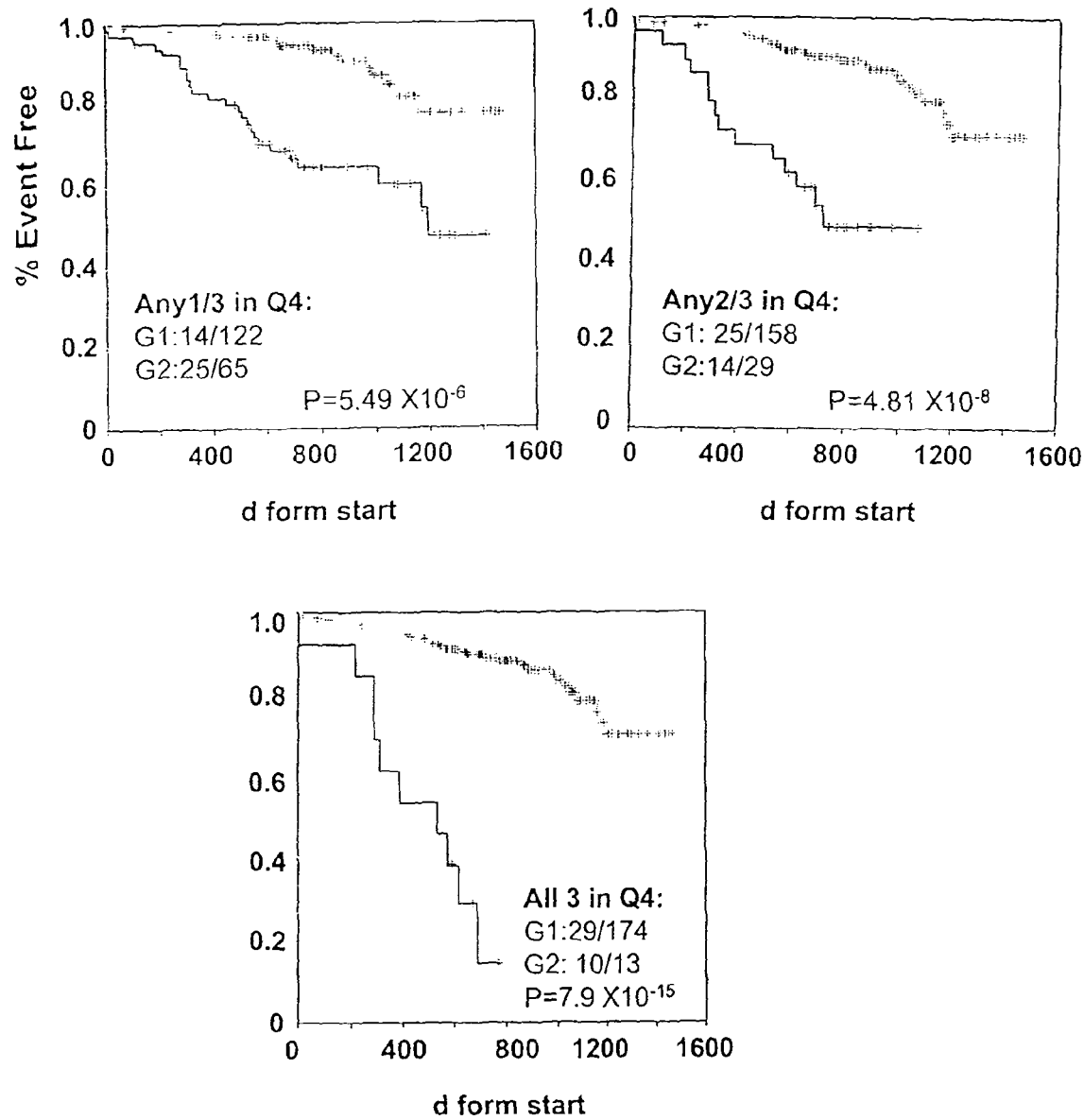
FIG. 3B shows that grouping two or more of the genes ASPM, OPN3 and CSK1B increases the power of predicting event-free survival.
Figure 4:
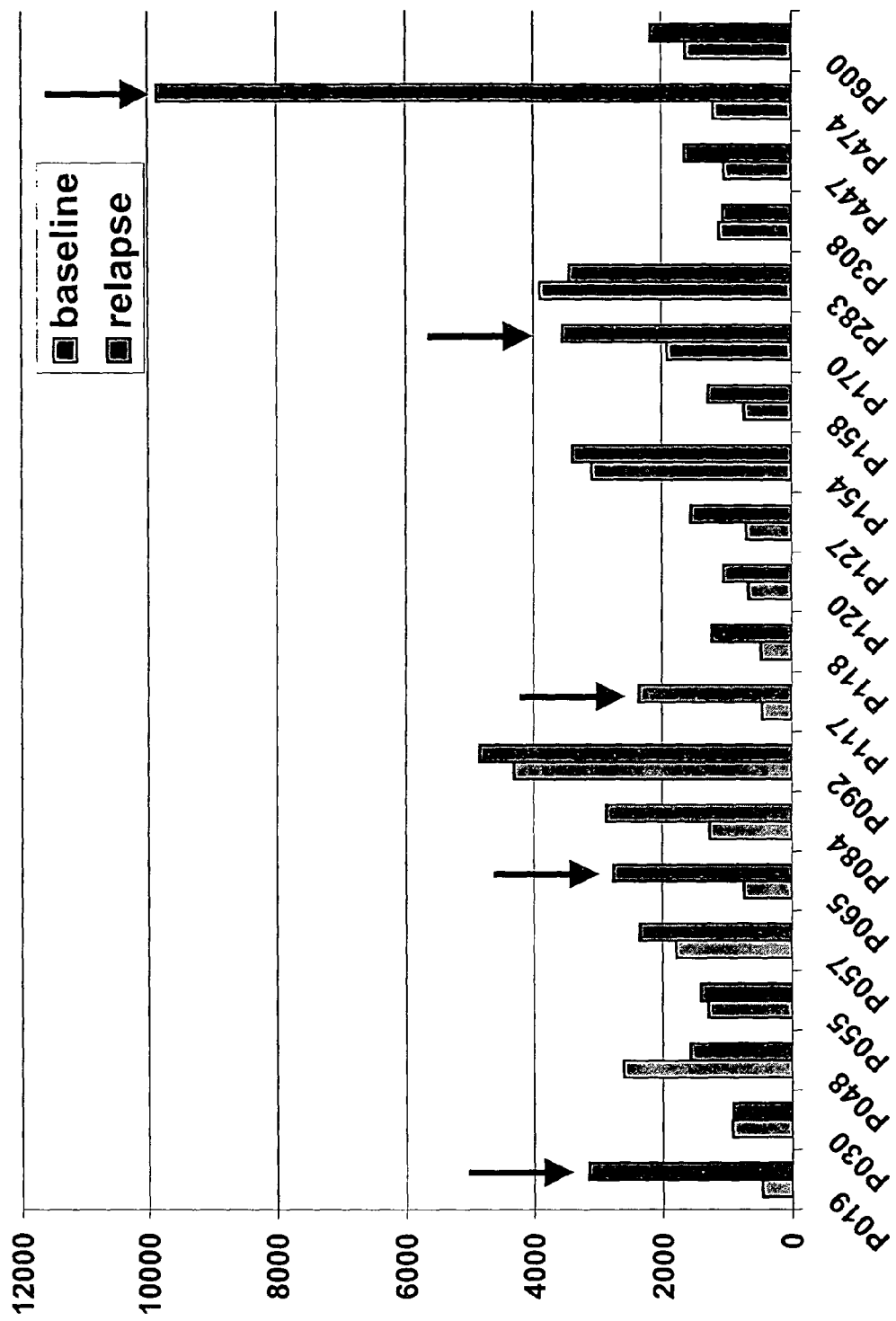
FIG. 4 shows increase of CSK1B expression and copy number was associated with relapse.

These three genes capable of predicting overall survival can also be used to predict event-free survival (FIG. 3A), and the power of prediction was increased by grouping two or more of the three genes in the analysis (FIG. 3B). FIG. 4 shows increase of CSK1B expression and copy number was associated with relapse.

TABLE 1

Seventeen Genes Whose Expression Levels Predict Early Death From Multiple Myeloma

| Probe Set | Gene Symbol | Chromosome |
| --- | --- | --- |
| 1565951_s_at | OPN3 | 1q43 |
| 200850_s_at | AHCYL1 | 1p12 |
| 201897_s_at | CKS1B | 1q21.2 |
| 201921_at | GNG10 | 9q32 |
| 202345_s_at | FABP5 | 8q21.13 |

TABLE 1-continued

Seventeen Genes Whose Expression Levels Predict Early Death From Multiple Myeloma

| Probe Set | Gene Symbol | Chromosome |
| --- | --- | --- |
| 202729_s_at | LTBP1 | 2p22-p21 |
| 206513_at | AIM2 | 1q22 |
| 208540_x_at | S100A11 | 1q21 |
| 209717_at | EVI5 | 1p22 |
| 210427_x_at | ANXA2 | 15q21-q22 |
| 213704_at | RABGGTB | 1p31 |
| 219918_s_at | ASPM | 1q31 |
| 222495_at | AD-020 | 1p13.3 |
| 224847_at | CDK6 | 7q21 |
| 227525_at | GLCCl1 | 7p22.1 |
| 230100_x_at | PAK1 | 11q13-q14 |
| 242488_at | | 1q43 |

Example 2

Gene Expression Profiling to Identify Candidate Genes as Diagnostic, Prognostic and Potential Targets of High-Risk Phenotype As discussed above, global gene expression profile identified genes whose over-expression or lack of expression could be useful for staging and performing a disease follow-up for multiple myeloma and other cancers. This gene profiling was also used to identify genes whose abnormal expression might cause high-risk phenotype of myeloma.

(a) Subjects:

668 newly diagnosed patients with symptomatic or progressive multiple myeloma were enrolled in the study, which included 2 cycles of blood stem cell-supported high-dose melphalan (200 mg/m$^2$) (Shaughnessy et al., 2003). A subset of 575 patients with available genetic measurements, as described below, constituted the sample for this analysis. Their median follow-up was 30 months. There were 185 progression or death events and 128 deaths. Patient characteristics were as follows: 20% were 65 years or older, 31% had beta-2-microglobulin levels $>=4$ mg/L, 55% had C-reactive protein levels $>=4$ mg/L; 22% presented with hemoglobin values $<=10$ g/dL, 10% with creatinine values $>=2$ mg/dL; LDH was elevated ($>=190$ IU/L) in 30%, albumin decreased ($<3.5$ g/dL) in 15%; cytogenetic abnormalities were detected in 33%. The median follow-up for survival in this subset was 22 months and there were 98 events and 64 deaths.

(b) Gene Expression Profiling:

Gene expression profiling, using the Affymetrix U133Plus2.0 microarray, was performed on CD138-enriched plasma cells isolated from 351 consecutive patients, as previously described (Zhan et al., 2002).

(c) Fluorescence In-Situ Hybridization (FISH):

Bacterial artificial chromosomes encompassing CKS1B at 1q21 (RP11-307C12) and ASPM (RP11-32D17) at 1q31 were purchased from BAC/PAC Resources (Oakland, Calif.) and directly labeled with Spectrum-Green or Spectrum-Red (Vysis Inc, Downers Grove, Ill.). Metaphase fluorescence in situ hybridization was performed as previously described (Sawyer et al., 2005). The probes were confirmed to map to the 1q21 and 1q31 bands using metaphase spreads from normal human lymphocytes. Triple color interphase fluorescence in situ hybridization analyses of chromosomes 13

(D13S31) and 1q21 (CKS1B) copy number were performed as described (Shaughnessy et al., 2000) in a subset of 421 patients (145 events and 100 deaths, follow-up of 31 months); deletion 13q was scored positive when >=80% of clonal cells exhibited loss of a signal at 13q14 as described (McCoy et al., 2003). Of these 421 patients, 197 were among those with microarrays and 224 were not.

(d) Western Blotting:

Nuclear protein was isolated from an aliquot of CD138 enriched plasma cells that were also analyzed by microarray. Western blotting was carried using the WesternBreeze® Chemiluminescent immunodetection protocol as described (Invitrogen, Carlsbad, Calif.). The antibodies to CKS1B and phospo-thr-187-CDKN1B were purchased from Zymed Laboratories Inc, (South San Francisco, Calif.) and anti-Histone 1A was purchased from Upstate Biotechnology (Charlottesville, Va.).

(e) CKS1B siRNA:

A synthetic double-stranded oligonucleotide sequence (5'-GATCCCCGGACATAGCCAAGCTGGTCTTCAAGAGA-GACCAGCTTGGCTATGTCCTTTTTA (SEQ ID NO. 1) (Kitajima et al., 2004), corresponding to a 19-nt sequence from CKS1B (nucleotide 78-96; OligoEngine, Seattle, Wash.) and a scrambled oligonucleotide (control) were used. CKS1B siRNA double stranded oligonucleotides were cloned into lentiviral vectors. Recombinant lentivirus were produced by transient transfection of 293T cells (ATCC) following a standard protocol (Zufferey et al., 1997). Crude virus was concentrated by ultracentrifugation at 26,000 rpm for 90 minutes. For viral titration, HeLa cells were transduced with viral stocks in various concentrations. After 72 hours incubation, titration was determined by determining the number of GFP expressing cells using flow cytometry. About $10^9$ transducing units (TU)/ml of viral titers were achieved. For transduction of myeloma cells, 20-30 TU/cells were added with 8 mg/ml of polybrene (Sigma), achieving >95% transduction efficiency. For determination of growth rates, $1\times10^4$ cells were cultured in triplicate wells in 96 well plates, and growth determined using the MTT assay (Sigma).

(f) Statistical Analysis:

The sample of 351 Affymetrix U133Plus2.0 microarrays were preprocessed using MAS5.01 software and normalized using conventional MAS5.01 scaling. Log rank tests for univariate association with disease-related survival were performed for each of the 54,675 'Signal' summaries. Specifically, log rank tests were performed for quartile 1 vs. quartiles 2-4 and quartile 4 vs. quartiles 1-3, in order to identify under- and over-expressed genes, respectively. A false discovery rate cut-off of 2.5% was applied to each list of log-rank P-values (Storey et al., 2003), yielding 19 under- and 51 over-expressed probe sets. For all 70, extreme quartile membership (Q1 or Q4) was associated with a higher risk of disease-related death. All other EFS and survival outcomes in this analysis were overall (i.e. not disease-related). The Kaplan-Meier method was used to estimate event-free and overall survival distributions and log rank tests were used to test for their equality across groups. Chi-square tests and Fisher's exact tests were used to test for the independence of categories. Multivariate proportional hazards regression was used to adjust the effects of CKS1B expression and amplification for other predictors, and the proportions of observed heterogeneity explained by the combined predictors (i.e. R2) were computed (O'Quigley and Xu et al., 2001). The statistical package R version 2.0 (R Development Core Team, 2004) was used for this analysis.

Microarray data for the 351 patients has been deposited in the NIH Gene Expression Omnibus under accession number GSE2658. Note that an analysis of baseline samples for 174 of the same patients was previously reported (De Vos et al., 2002) using Affymetrix U95Av2 microarrays. These samples were again hybridized to U133Plus2.0 microarrays for the current analyses.

Figure 6A:
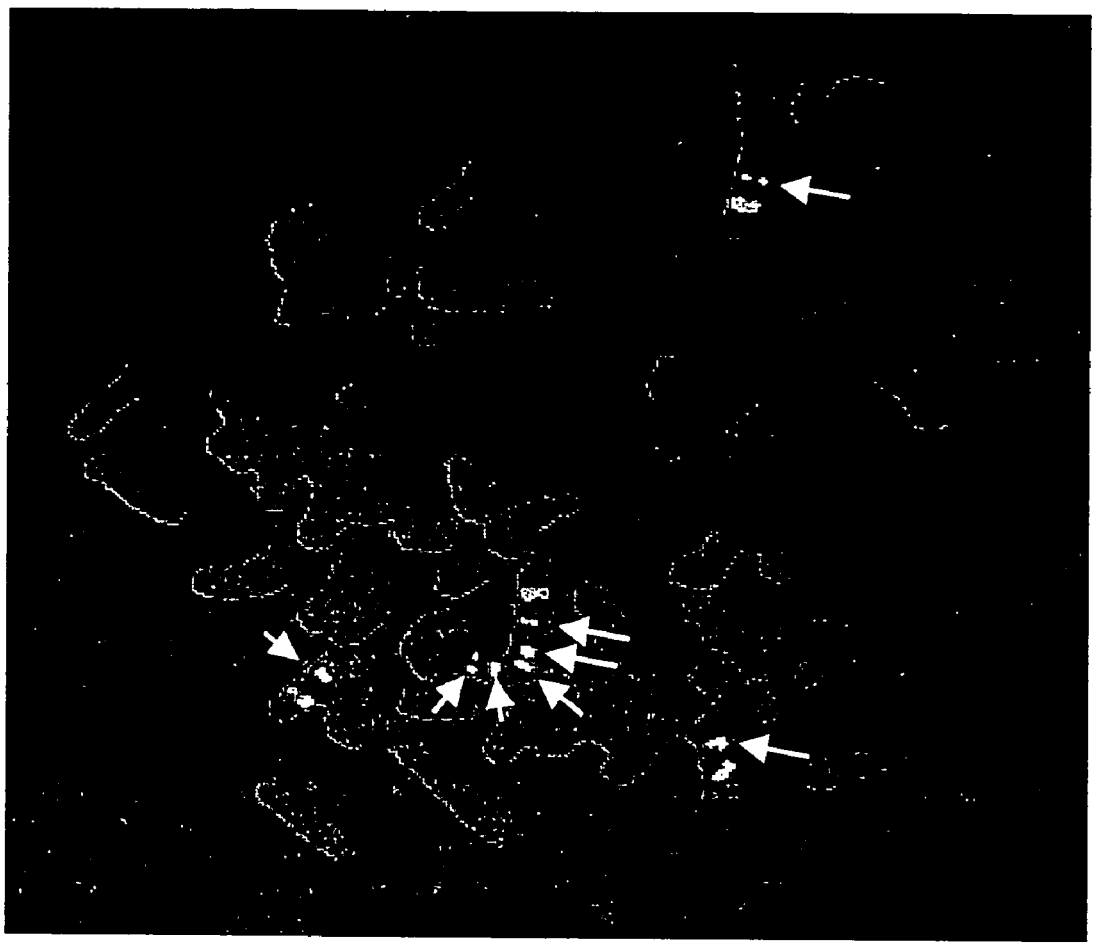
FIGS. 6A-D show that increased CKS1B expression is related to increased CKS1B DNA copy number and the degree of DNA amplification is linked to poor survival.
Figure 6B:
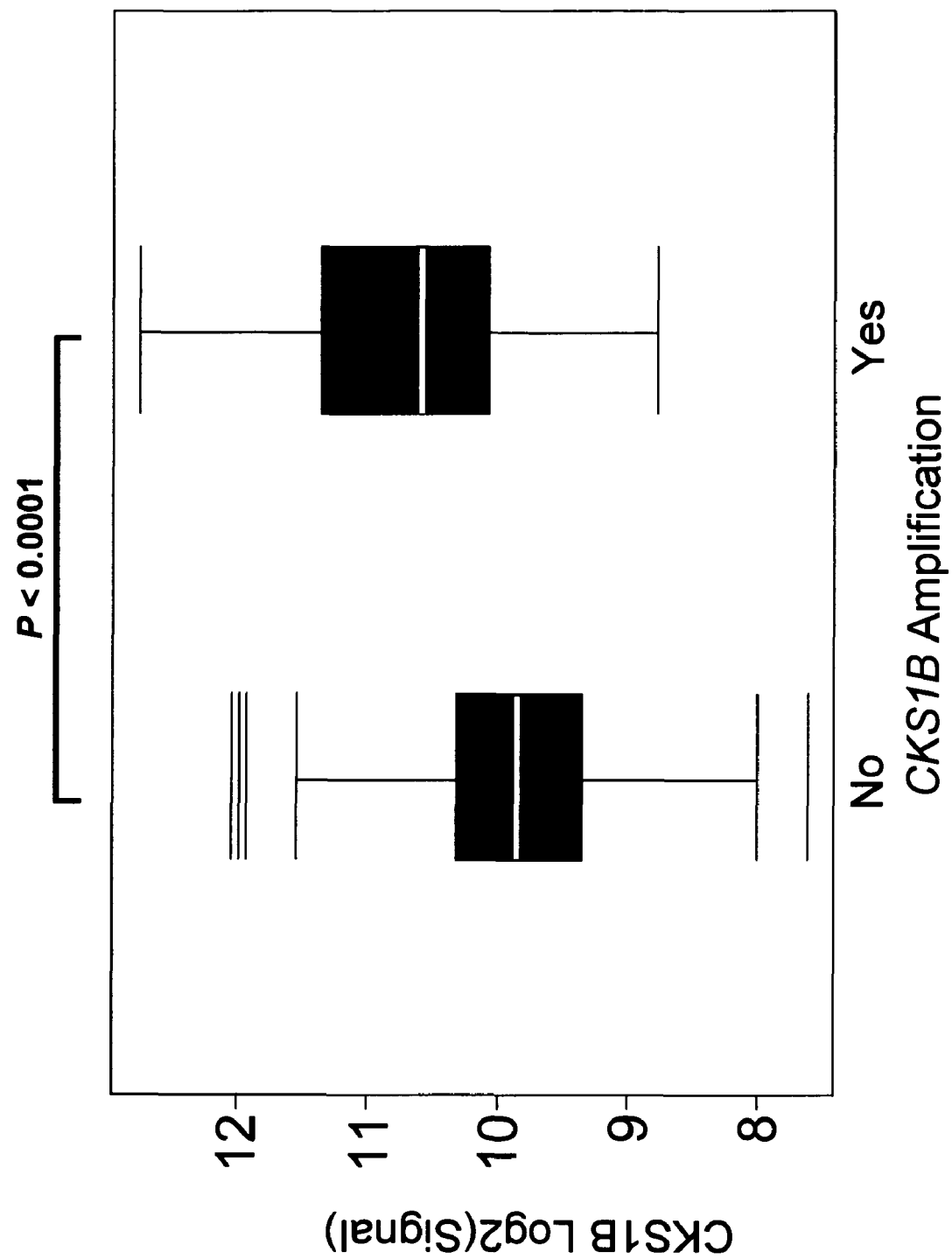
Figure 6C:
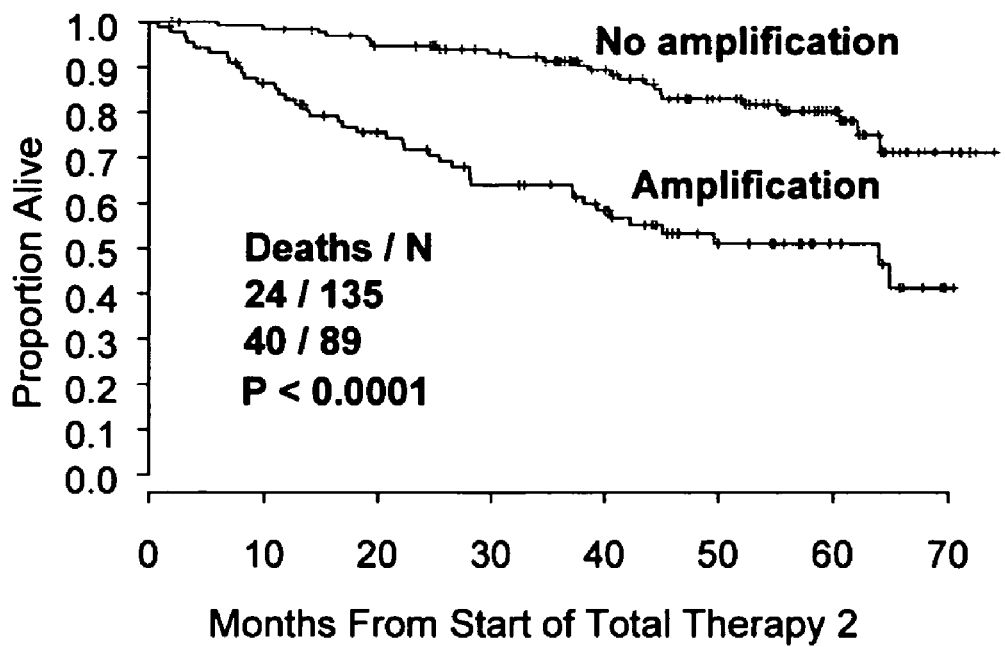
Figure 6D:
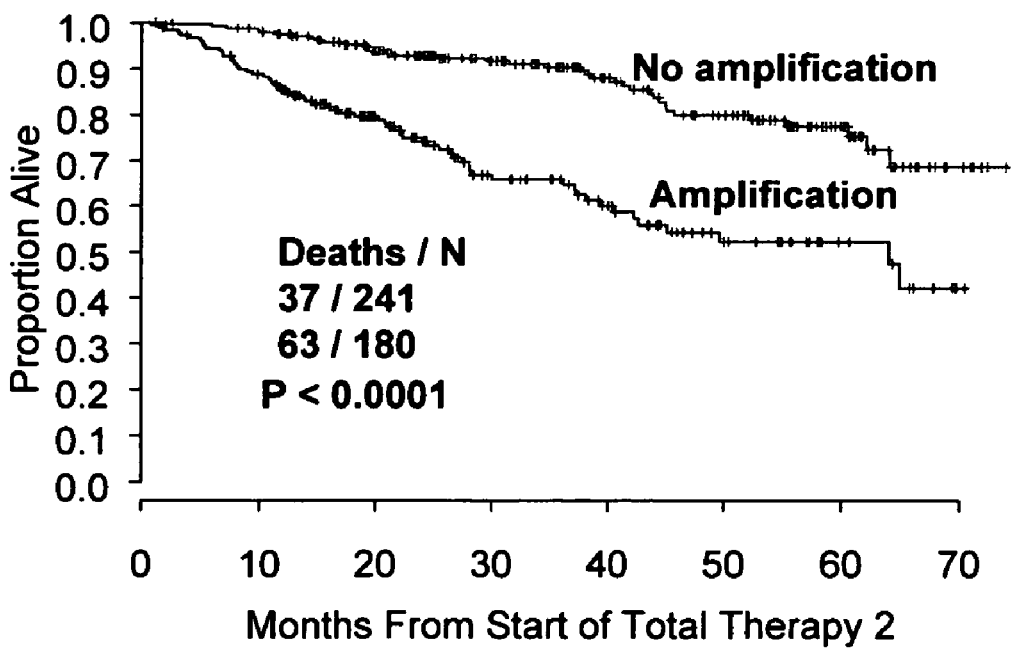

(g) FISH-Based CKS1B Amplification Index:

A conventional, laboratory-defined cutoff of 20% for the proportion of clonal plasma cells with 3 signals or >=4 signals was used for tests of association between expression and amplification (FIG. 6B and Table 5) and for validation of the association between amplification and overall survival (FIGS. 6C-D). Hypothesizing that 2 or more extra copies would confer additional risk compared to 1 extra copy, the multivariate analysis of overall survival (Table 4A) estimated separate effect sizes for the 3 signal proportion and the >=4 signal proportion. These effect sizes were used to define the amplification index as a weighted sum: (0.34*% 3 Copies+ 0.66*%>=4 Copies)/0.66. The index is scaled so that it increases by one for each unit increase in the proportion with >=4 signals. The index is 0 for patients with <=2 signals in 100% of clonal cells, 51.5% for patients with 3 signals in 100%, and 100 for patients with >=4 signals in 100%. The full range was observed in these patients. A cutoff for the index of >=46 minimized the unadjusted log rank P-value for survival in the 421 patient subset (i.e. an optimal cutoff). Note that all cutoffs for the index between 3 and 88 had P<0.003.

(h) Genetic Sub Groups:

Nearly 50% of newly diagnosed myelomas contain one of five recurrent chromosomal translocations that result in the hyper-activation of MAF, MAFB, FGFR3/MMSET, CCND3, CCND1 (Kuehl et al., 2002) with divergent prognoses (Fonseca et al., 2004), detectable as "spiked" expression by microarray analysis (Valk et al., 2004). Genetic subgroups were classified based on presence or absence of these translocation spikes. Patients were also classified within the context of metaphase cytogenetics as having normal karyotypes (originating in normal hematopoietic cells in case of hypoproliferative myeloma) or as having hyperdiploid, hypodiploid or "other" cytogenetic abnormalities. "Other" is defined as an abnormal metaphase karyotype, i.e. structural and/or numeric changes, with a diploid modal chromosome number. Thus, different from the Paris workshop (Fonseca et al., 2004), non-translocation entities were defined by metaphase rather than interphase cytogenetics.

(i) Microarray Analysis:

Affymetrix MAS5.01 preprocessed 'Signal' summaries were used exclusively for this analysis, with MAS5.01 array normalization performed by scaling the 2% trimmed mean of each array's probe set signals to equal 500. To select focus genes, a single criterion was used for both probe set filtering and significance analysis as an outgrowth of the particular experimental design. Rather than comparing continuous expression levels across pre-defined categories, as is often the case, the design called for comparing the distribution of early disease-related death (median follow-up <2 years) across quartiles of the expression distribution. The design was informed by the biological hypothesis that poor-prognosis genes which are "switched" off or on may be associated with expression in the lower or upper quartile of the sample, respectively. Log rank tests for disease-related survival differences across Q1 vs. other and Q4 vs. other were performed for all 54,675 probe set signals, with the single restriction that the sample contained sufficient unique signal values for the probe set, a condition met by all (i.e. a minimum of 79 unique values). Among the 70 probe sets declared significant for under- or over-expression, the minimum number of unique values was 323 (30$^{th}$ percentile of the 54,675) and the median was 346 (83$^{rd}$ percentile). The minimum sample variance of the log base 2 signals was 0.13 (0.6$^{th}$ percentile) and the median was 0.52 (29th percentile). The minimum fold change over the signal range was 2.13 (0.4[th] percentile) and the median was 5.26 (40th percentile). Examination of the expression distributions of probes sets declared significant suggested no reason why any of them should be "filtered" out by minimum variance or fold change filters, particular since the largest log rank P-value was 0.00003. Significance analysis was performed by computing estimates of the false discovery rates that correspond to specified P-value cutoffs, as described by Storey and Tibshirani (Shaughnessy et al., 2003). The 70 gene list is based upon P-value cutoffs with estimated false discovery rates of 2.5% for the under- and over-expressed P-value lists.

Example 3

Results of the Global Gene Expression Profiling

On a molecular basis to identify genes that might contributed to high-risk myeloma, gene expression profiles of purified plasma cells were correlated with disease-related and overall survival in 351 newly diagnosed patients treated with 2 cycles of high-dose melphalan.

Using log rank tests, 70 genes were identified for which fourth or first quartile membership was correlated with a high incidence of disease-related death (Table 2). Although 10% of the genes on the microarray were derived from chromosome 1, 30% of the retained genes were derived from this chromosome (P<0.0001); 9 of 51 quartile 4 genes mapped to chromosome arm 1q and 2 to arm 1p whereas 9 of 19 quartile 1 genes mapped to chromosome arm 1p and none on arm 1q (Table 3). The over-representation of 1q genes among the list of 70 and the observation that amplification of 1q21 was associated with progression and poor prognosis in myeloma (Smadja et al., 2001; Sawyer et al., 2005; Philip et al., 1980) justified a focus on this region in search for a molecular basis of high-risk myeloma: 2 genes (PSMD4 and CKS1B) map to 1q21, among which CKS1B quartile 4 membership was most strongly associated with survival in unadjusted log rank tests (Table 2).

TABLE 2A

Quartile 4 FDR 2.5% gene probe sets - rank correlations with 1q21 amplification index, CKS1B and PC labeling index and adjusted P-values for associations with overall survival

| Rank (Q4) | Chromosome | Probe set | Symbol | CKS1B Amplification Index r[†] | CKS1B r[‡] | PCLI r[*] | Adjusted Survival P-value[a] |
|---|---|---|---|---|---|---|---|
| 1 | 8q21.13 | 202345_s_at | NA | 0.20 | 0.22 | | 0.001 |
| 2 | Xp22.2-p22.1 | 1555864_s_at | NA | 0.34 | 0.47 | | 0.007 |
| 3 | 5p15.33 | 204033_at | TRIP13 | 0.19 | 0.45 | 0.20 | 0.001 |
| 4 | 1q22 | 206513_at | AIM2 | 0.15 | 0.13 | | 0.089 |
| 5 | 2p24.1 | 1555274_a_at | SELI | 0.28 | 0.31 | | 0.001 |
| 6 | 21q22.3 | 211576_s_at | SLC19A1 | 0.17 | 0.23 | | 0.007 |
| 7 | 3p21.3 | 204016_at | LARS2 | −0.18 | | | 0.002 |
| 8 | 1q43 | 1565951_s_at | OPN3 | 0.36 | 0.36 | | 0.007 |
| 9 | 1q31 | 219918_s_at | ASPM | 0.36 | 0.64 | 0.17 | 0.010 |
| 10 | 12q15 | 201947_s_at | CCT2 | 0.23 | 0.43 | 0.13 | 0.004 |
| 11 | 16p13.3 | 213535_s_at | UBE2I | | 0.38 | | 0.022 |
| 12 | 20q13.2-q13.3 | 204092_s_at | STK6 | 0.31 | 0.51 | 0.19 | 0.044 |
| 13 | 1p36.33-p36.21 | 213607_x_at | FLJ13052 | | | | 0.150 |
| 14 | xq12-q13 | 208117_s_at | FLJ12525 | | 0.34 | | 0.006 |
| 15 | 17q25 | 210334_x_at | BIRC5 | 0.20 | 0.36 | 0.14 | 0.110 |
| 16 | 3q27 | 204023_at | NA | 0.29 | 0.62 | 0.16 | 0.072 |
| 17 | 1q21.2 | 201897_s_at | CKS1B | 0.50 | 1.00 | 0.15 | 0.007 |
| 18 | 19q13.11-q13.12 | 216194_s_at | CKAP1 | 0.24 | 0.38 | | 0.001 |
| 19 | 1q21 | 225834_at | MGC57827 | 0.39 | 0.66 | 0.23 | 0.140 |
| 20 | 19q13.12 | 238952_x_at | DKFZp779O175 | | 0.11 | | 0.009 |
| 21 | 17p13.3 | 200634_at | PFN1 | 0.30 | 0.41 | | 0.002 |
| 22 | 19p13.2 | 208931_s_at | ILF3 | 0.22 | 0.22 | | 0.220 |
| 23 | 1q22 | 206332_s_at | IFI16 | 0.30 | 0.32 | 0.13 | 0.003 |
| 24 | 7p14-p13 | 220789_s_at | TBRG4 | | 0.13 | 0.17 | 0.009 |
| 25 | 10p11.23 | 218947_s_at | PAPD1 | 0.31 | 0.30 | | 0.150 |
| 26 | 8q24 | 213310_at | EIF2C2 | 0.28 | 0.37 | | 0.031 |
| 27 | 3q12.1 | 224523_s_at | MGC4308 | 0.17 | 0.24 | 0.14 | 0.038 |
| 28 | 1p36.3-p36.2 | 201231_s_at | ENO1 | | 0.23 | | <0.001 |
| 29 | 18q12.1 | 217901_at | DSG2 | 0.15 | | | 0.005 |
| 30 | 6q22 | 226936_at | NA | 0.15 | 0.52 | 0.17 | 0.027 |
| 31 | 8q24.3 | 58696_at | EXOSC4 | | 0.20 | | 0.330 |
| 32 | 1q21-q25 | 200916_at | TAGLN2 | 0.47 | 0.52 | | 0.120 |
| 33 | 3q21 | 201614_s_at | RUVBL1 | 0.16 | 0.14 | | 0.023 |
| 34 | 16q22-q24 | 200966_x_at | ALDOA | 0.21 | 0.28 | | 0.001 |
| 35 | 2p25.1 | 225082_at | CPSF3 | | 0.39 | | 0.073 |
| 36 | 1q43 | 242488_at | NA | 0.18 | 0.27 | 0.14 | 0.090 |
| 37 | 3q12.3 | 243011_at | MGC15606 | | 0.27 | | 0.004 |
| 38 | 22q13.1 | 201105_s_at | LGALS1 | | 0.31 | | 0.051 |
| 39 | 3p25-p24 | 224200_s_at | RAD18 | 0.17 | 0.41 | 0.14 | 0.040 |
| 40 | 20p11 | 222417_s_at | SNX5 | | | | 0.085 |
| 41 | 1q21.2 | 210460_s_at | PSMD4 | 0.58 | 0.59 | 0.13 | 0.067 |
| 42 | 12q24.3 | 200750_s_at | RAN | 0.22 | 0.40 | | 0.056 |
| 43 | 1pter-q31.3 | 206364_at | KIF14 | 0.41 | 0.57 | 0.25 | 0.019 |
| 44 | 7p15.2 | 201091_s_at | CBX3 | 0.14 | 0.20 | 0.16 | 0.150 |
| 45 | 12q22 | 203432_at | TMPO | 0.32 | 0.59 | 0.18 | 0.007 |

TABLE 2A-continued

Quartile 4 FDR 2.5% gene probe sets - rank correlations with 1q21 amplification index, CKS1B and PC labeling index and adjusted P-values for associations with overall survival

| Rank (Q4) | Chromosome | Probe set | Symbol | CKS1B Amplification Index $r^†$ | CKS1B $r^‡$ | PCLI $r^*$ | Adjusted Survival P-value$^a$ |
|---|---|---|---|---|---|---|---|
| 46 | 17q24.2 | 221970_s_at | DKFZP586L0724 | 0.27 | 0.47 | | 0.081 |
| 47 | 11p15.3-p15.1 | 212533_at | WEE1 | 0.20 | 0.54 | 0.13 | 0.056 |
| 48 | 3p12 | 213194_at | ROBO1 | | | | 0.150 |
| 49 | 5q32-q33.1 | 244686_at | TCOF1 | | | | 0.120 |
| 50 | 8q23.1 | 200638_s_at | YWHAZ | 0.26 | 0.23 | | 0.012 |
| 51 | 10q23.31 | 205235_s_at | MPHOSPH1 | | 0.40 | 0.16 | 0.050 |

TABLE 2B

Quartile 1 gene probe sets satisfying FDR 2.5% cutoff

| Rank (Q1) | Chromosome | Probe set | Symbol | CKS1B Amplification Index $r^†$ | CKS1B $r^‡$ | PCLI $r^*$ | Adjusted Survival P-value$^a$ |
|---|---|---|---|---|---|---|---|
| 1 | 9q31.3 | 201921_at | GNG10 | −0.20 | −0.30 | | 0.600 |
| 2 | 1p13 | 227278_at | NA | | | −0.12 | 0.900 |
| 3 | Xp22.3 | 209740_s_at | PNPLA4 | | | | 0.029 |
| 4 | 20q11.21 | 227547_at | NA | −0.29 | −0.28 | −0.15 | 0.630 |
| 5 | 10q25.1 | 225582_at | KIAA1754 | −0.21 | −0.32 | | 0.003 |
| 6 | 1p13.2 | 200850_s_at | AHCYL1 | | | −0.13 | 0.019 |
| 7 | 1p13.3 | 213628_at | MCLC | −0.30 | −0.28 | −0.15 | 0.440 |
| 8 | 1p22 | 209717_at | EVI5 | −0.33 | −0.29 | −0.16 | 0.870 |
| 9 | 1p13.3 | 222495_at | AD-020 | −0.30 | −0.24 | −0.20 | 0.920 |
| 10 | 6p21.31 | 1557277_a_at | NA | | −0.11 | | 0.460 |
| 11 | 1p22.1 | 1554736_at | PARG1 | | −0.20 | −0.11 | 0.280 |
| 12 | 1p22 | 218924_s_at | CTBS | −0.16 | −0.11 | −0.13 | 0.460 |
| 13 | 9p13.2 | 226954_at | NA | −0.22 | −0.40 | | 0.090 |
| 14 | 1p34 | 202838_at | FUCA1 | −0.17 | −0.23 | | 0.066 |
| 15 | 13q14 | 230192_at | RFP2 | −0.28 | −0.18 | | 0.880 |
| 16 | 12q13.11 | 48106_at | FLJ20489 | −0.23 | −0.23 | −0.11 | 0.300 |
| 17 | 11q13.1 | 237964_at | NA | −0.16 | −0.20 | | 0.044 |
| 18 | 2p22-p21 | 202729_s_at | LTBP1 | −0.24 | −0.21 | | 0.097 |
| 19 | 1p13.1 | 212435_at | NA | −0.21 | −0.21 | −0.11 | 0.034 |

$^†$Correlation between each gene's log-scale expression and the CKS1B amplification index (N = 197, all patients with both GEP and FISH 1q21). Blank cells correspond to correlations with P > 0.05.
$^‡$Correlation between each gene's log-scale expression and CKS1B log-scale expression (N = 351, all patients with GEP). Rows with CKS1B |r| >= 0.4 are formatted bold.
$^*$Correlation between each gene's log-scale expression and the PCLI (N = 305, 46 patients are missing PCLI).
$^a$Multivariate proportional hazards regression of overall survival on extreme quartile expression (Q1 or Q4) for each gene, adjusted for FISH 13 80%, cytogenetic abnormalities, B2M > 4, CRP > 4, ALB < 3.5 and PCLI (N = 277, 74 patients are missing at least one measurement).

TABLE 3

Chromosome distribution of 2.5% FDR gene probe sets

| | U133Plus2.0 | | Q1 | | Q4 | | Combined | | |
|---|---|---|---|---|---|---|---|---|---|
| Chromosome | Number of Genes | % | Number of Genes | % | Number of Genes | % | Number of Genes | % | P value* |
| 1 | 3,659 | 9.9 | 9 | 47.4 | 12 | 23.5 | 21 | 30.0 | <0.0001 |
| 2 | 2,522 | 6.9 | 1 | 5.3 | 2 | 3.9 | 3 | 4.3 | |
| 3 | 2,116 | 5.8 | 0 | 0.0 | 7 | 13.7 | 7 | 10.0 | |
| 4 | 1,456 | 4.0 | 0 | 0.0 | 0 | 0.0 | 0 | 0.0 | |
| 5 | 1,718 | 4.7 | 0 | 0.0 | 2 | 3.9 | 2 | 2.9 | |
| 6 | 2,005 | 5.4 | 1 | 5.3 | 1 | 2.0 | 2 | 2.9 | |
| 7 | 1,798 | 4.9 | 0 | 0.0 | 2 | 3.9 | 2 | 2.9 | |
| 8 | 1,311 | 3.6 | 0 | 0.0 | 4 | 7.8 | 4 | 5.7 | |
| 9 | 1,463 | 4.0 | 2 | 10.5 | 0 | 0.0 | 2 | 2.9 | |
| 10 | 1,444 | 3.9 | 1 | 5.3 | 2 | 3.9 | 3 | 4.3 | |
| 11 | 2,069 | 5.6 | 1 | 5.3 | 1 | 2.0 | 2 | 2.9 | |
| 12 | 1,927 | 5.2 | 1 | 5.3 | 3 | 5.9 | 4 | 5.7 | |
| 13 | 730 | 2.0 | 1 | 5.3 | 0 | 0.0 | 1 | 1.4 | |

TABLE 3-continued

Chromosome distribution of 2.5% FDR gene probe sets

| Chromosome | U133Plus2.0 Number of Genes | % | Q1 Number of Genes | % | Q4 Number of Genes | % | Combined Number of Genes | % | P value* |
|---|---|---|---|---|---|---|---|---|---|
| 14 | 1,195 | 3.2 | 0 | 0.0 | 0 | 0.0 | 0 | 0.0 | |
| 15 | 1,152 | 3.1 | 0 | 0.0 | 0 | 0.0 | 0 | 0.0 | |
| 16 | 1,507 | 4.1 | 0 | 0.0 | 2 | 3.9 | 2 | 2.9 | |
| 17 | 2,115 | 5.7 | 0 | 0.0 | 3 | 5.9 | 3 | 4.3 | |
| 18 | 582 | 1.6 | 0 | 0.0 | 1 | 2.0 | 1 | 1.4 | |
| 19 | 2,222 | 6.0 | 0 | 0.0 | 3 | 5.9 | 3 | 4.3 | |
| 20 | 1,072 | 2.9 | 1 | 5.3 | 2 | 3.9 | 3 | 4.3 | |
| 21 | 468 | 1.3 | 0 | 0.0 | 1 | 2.0 | 1 | 1.4 | |
| 22 | 906 | 2.5 | 0 | 0.0 | 1 | 2.0 | 1 | 1.4 | |
| X | 1,273 | 3.5 | 1 | 5.3 | 2 | 3.9 | 3 | 4.3 | |
| Y | 80 | 0.2 | 0 | 0.0 | 0 | 0.0 | 0 | 0.0 | |
| m | 5 | 0.0 | 0 | 0.0 | 0 | 0.0 | 0 | 0.0 | |
| | 36,795 | | 19 | | 51 | | 70 | | |
| Unknown | 17,880 | | | | | | | | |
| | 54,675 | | | | | | | | |

*An exact test for binomial proportions was used to compare the proportion of retained probe sets mapping to chromosome 1 to the proportion for the entire array.

The log-scale expression levels of proliferation-associated genes tended to have high correlations with CKS1B (Table 2). In addition, 25 of 29 (86%) genes, significantly correlated with the plasma cell labeling index, were strongly correlated with CKS1B, suggesting that this gene participated in a proliferation signaling network in patients with high risk disease. CKS1B was an independent predictor of overall survival after adjustment for chromosome 13 deletion by interphase FISH, metaphase cytogenetic abnormalities, clinical prognostic factors and labeling index (P=0.007, Table 2, last column, row 17). Adjusted P-values are provided for the other 69 genes for comparison, and it was evident that few other chromosome 1 genes are both strong independent predictors of survival, proliferation, and CKS1B gene amplification.

Although the median age of the present cohort was 57, younger than the median age at diagnosis, the 25% between 64 and 76 were sufficient to consider whether age modified the effect of CKS1B over-expression or amplification in the multivariate analyses in Tables 2 and 4b, respectively. As a continuous variable, age was not a significant modifier of CKS1B's effect on survival in either analysis (P=0.37, HR 1.03, for CKS1B expression and P=0.81, HR 0.99, for amplification), with the strongest effect corresponding to an estimated 3% higher hazard for an additional 1 year in age (results are similar for EFS). Additionally, there was a slightly higher prevalence of CKS1B amplification among patients 65 and older (P=0.2). It was speculated that genes associated with the 1q21-mediated proliferation pathway dominated as univariate predictors of disease-related survival in early follow-up. Genes related to other genetic lesions, such as FGFR3/MMSET, MAF and MAFB ranked below the 70, but might appear at higher false discovery rates.

TABLE 4

Multivariate proportional hazards analysist†(n = 369)

| | % | Event-Free Survival | | | Survival | | |
|---|---|---|---|---|---|---|---|
| | | HR | P | Cumulative $r^2$ | HR | P | Cumulative $r^2$ |
| A. | | | | | | | |
| CKS1B Amplification Index (0-100) | | 1.009 | 0.002 | 0.160 | 1.011 | 0.002 | 0.219 |
| FISH Chromosome 13 Deletion | 25.5 | 1.786 | 0.006 | 0.224 | 1.879 | 0.014 | 0.308 |
| Abnormal Karyotype | 35.0 | 1.875 | 0.001 | 0.272 | 2.298 | <0.001 | 0.393 |
| Beta-2-microglobulin >= 4 mg/L | 35.8 | 1.478 | 0.046 | 0.305 | 1.396 | 0.170 | 0.422 |
| C-reactive protein >= 4 mg/L | 63.4 | 1.533 | 0.028 | 0.320 | 1.586 | 0.055 | 0.448 |
| Albumin < 3.5 g/dL | 16.5 | 1.660 | 0.019 | 0.336 | 1.698 | 0.044 | 0.461 |
| Events/Deaths | | | | 127 | | | 84 |
| B. | | | | | | | |
| CKS1B Amplification Index >= 46 | 32.5 | 1.68 | 0.008 | 0.132 | 2.12 | 0.001 | 0.207 |

TABLE 4-continued

Multivariate proportional hazards analysist[†](n = 369)

| | | Event-Free Survival | | | Survival | | |
|---|---|---|---|---|---|---|---|
| | % | HR | P | Cumulative $r^2$ | HR | P | Cumulative $r^2$ |
| FISH Chromosome 13 Deletion | 25.5 | 1.74 | 0.010 | 0.204 | 1.83 | 0.020 | 0.293 |
| Abnormal Karyotype | 35.0 | 1.94 | <0.001 | 0.257 | 2.33 | <0.001 | 0.383 |
| Beta-2-microglobulin >= 4 mg/L | 35.8 | 1.52 | 0.033 | 0.293 | 1.43 | 0.140 | 0.417 |
| C-reactive protein >= 4 mg/L | 63.4 | 1.49 | 0.038 | 0.312 | 1.56 | 0.060 | 0.443 |
| Albumin < 3.5 g/d L | 16.5 | 1.69 | 0.016 | 0.331 | 1.73 | 0.035 | 0.455 |
| Events/Deaths | | | | 127 | | | 84 |

[†]369 of 421 patients with CKS1B amplification measurements had complete measurements for this analysis.) a) Multivariate proportional hazards analysis with the continuous CKS1B amplification index. A patient group with an index one unit larger than another has an estimated 0.9% higher risk of progression and 1.1% higher risk of death (i.e. an increase of approximately 1% in risk with each increase of 1 in the index). Labeling index was not significant in either analysis (P > 0.35, HR < 1.11, N = 325, EFS events = 116, deaths = 77, with 44 additional subjects missing the labeling index). b) Multivariate proportional hazards analysis with a cutoff of >= 46 for the CKS1B amplification index. Labeling index was not significant in either analysis (P > 0.32, HR < 1.12, N = 325).

Thus, based on its well-documented role in regulating cell cycle progression, its chromosome map location, link to myeloma cell proliferation and patient survival, CKS1B was considered a candidate gene, the inappropriate expression of which might promote an aggressive phenotype.

Figure 5A:
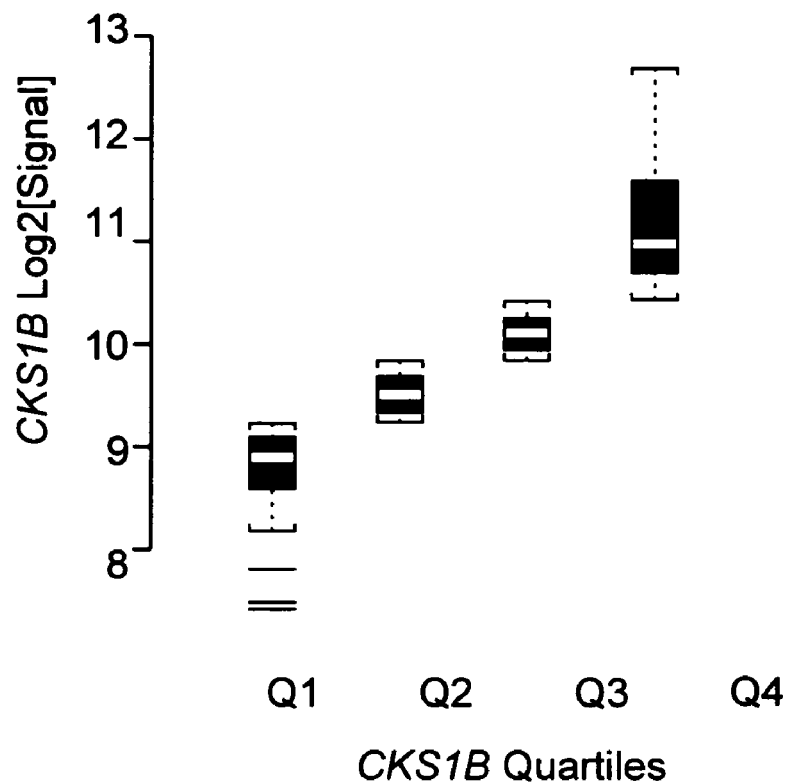
FIGS. 5A-B show that CKS1B expression by myeloma plasma cells varies and that high levels of expression of CKS1B define a high-risk myeloma entity.
Figure 5B:
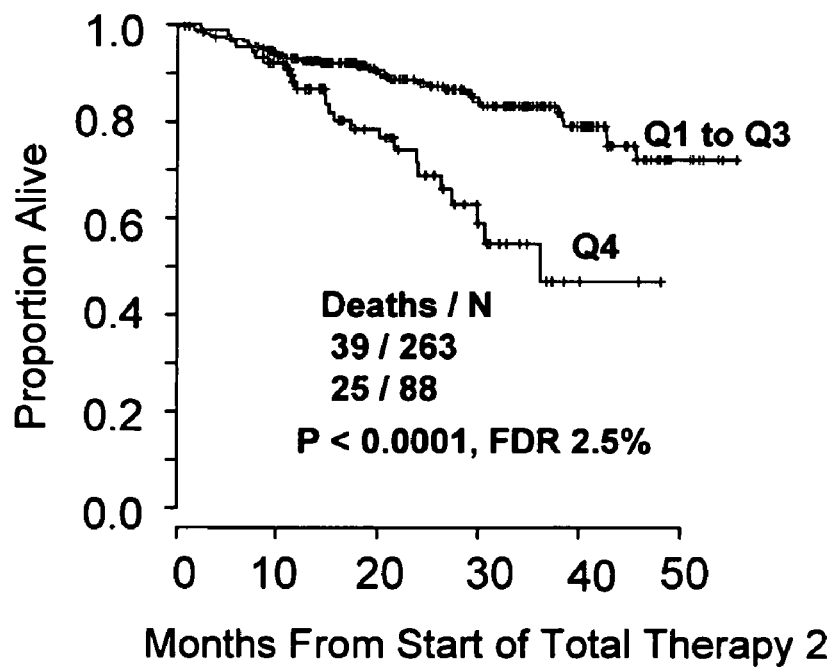

As was true for all the gene transcripts listed in Table 2, CKS1B levels were strongly correlated with clinical outcome (FIG. 5): 25 deaths had occurred among 88 patients with quartile 4 expression levels compared to only 39 among the 263 patients with quartile 1-3 levels (p<0.0001, false discovery rate, 2.5%); this was also true for event-free survival (34 of 88 in the quartile 4 cohort had experienced an event compared to 64 of 263 in the remainder; p<0.0001). Levels of SKP2, the CKS1B partner gene, were uniformly high and not significantly associated with survival (P=0.3).

Additionally, interphase FISH analysis revealed 3 or more copies of CKS1B in 46% among 197 cases with concurrent gene expression data. Expression levels were significantly linked to CKS1B copy number (FIG. 6B). Conversely, amplification increased in frequency as CKS1B expression levels increased from quartile 1 to quartile 4 (P<0.0001, Table 5). Examination of CKS1B gene amplification in the context of expression levels of the 70 genes (Table 2) revealed, as expected, correlations with genes on chromosome band 1q21 but, importantly, also with genes linked to cell proliferation not mapping to 1q21.

TABLE 5

Relationship between CKS1B gene expression quartiles and CKS1B amplification by interphase fluorescence in-situ hybridization in newly diagnosed myeloma.

| CKS1B Expression[†] | # AMPLIFIED | % AMPLIFIED |
|---|---|---|
| quartile 1[‡] n = 44 | 9 | 20% |
| quartile 2 n = 43 | 12 | 28% |
| quartile 3 n = 51 | 26 | 51% |

TABLE 5-continued

Relationship between CKS1B gene expression quartiles and CKS1B amplification by interphase fluorescence in-situ hybridization in newly diagnosed myeloma.

| CKS1B Expression[†] | # AMPLIFIED | % AMPLIFIED |
|---|---|---|
| quartile 4 n = 59 | | 75% |
| total | 91 | 46% |
| 197 | | |

[†]P < 0.0001. Amplification is defined as >= 20% of cells with 3 or >= 4 CKS1B signals, for validation in conjunction with FIG. 2c-d, as described in the Methods. Other tables use the CKS1B amplification index and its optimal cutoff.
[‡]Quartile assignments based upon 351 patients with GEP All myeloma cell lines expressed elevated levels of CKS1B and ASPM, mapping to 1q31 and in the list of 51 overexpressed genes linked to outcome in this analysis. Metaphase FISH for CKS1B and ASPM revealed 3- to 8-copies of CKS1B in 21 cell lines, whereas ASPM was amplified (3- to 6-copies) in only 16 cell lines (data not shown). Metaphase FISH of a primary myeloma (FIG. 6A) provided clear evidence of CKS1B amplification in the absence of ASPM amplification. Thus, even though overexpression of both genes was linked to survival and both genes map to the same chromosome band, CKS1B was more frequently amplified in myeloma than ASPM.

Next, the relationship between cytogenetic abnormalities involving chromosome 1q and CKS1B FISH was examined. In 414 primary cases with both abnormal cytogenetics and interphase FISH data for CKS1B amplification, CKS1B amplification was observed in 16 of 17 cases (94%) with 1q gain by cytogenetics, while CKS1B amplification was observed by interphase FISH in 61 of 112 cases lacking gross evidence of 1q abnormalities in spite of the presence of abnormal metaphase cytogenetics (data not shown). Taken together these data suggested that CKS1B amplification was not simply mirroring chromosome 1 trisomy.

The BAC clone used to evaluate CKS1B gene copy number also measured the copy number of PBXIP1 (mapping centromeric to CKS1B) and PB591, LENEP, ZFP67, FLJ32934, ADAM15 and EFNA4 (all mapping telomeric to CKS1B). In examining the relationship between gene copy number and the expression levels of these genes (Table 6), RNA expression was most strongly correlated with DNA copy number in the case of CKS1B. Importantly, none of the other genes mapping to this BAC were among the 70 linked to short survival. Moreover, the expression of candidate genes BCL9, MCL1, IL6R, and RAB25, that did not map to the BAC clone, but that did map to 1q21, were not linked to survival in this analysis (data not shown).

TABLE 6

Relationship of quartile 4 gene expression to amplification for genes located on bacterial artificial chromosome (BAC) used to measure 1q21 amplification

| Symbol | Not Amplified n/129 | (%) | Amplified* (Amplification. Index. >= 46) n/68 | (%) | P-Value[†] | Amplification Index r[‡] | Log Rank P-Value[a] |
|---|---|---|---|---|---|---|---|
| PBXIP1 | 24 | (18.6) | 28 | (41.2) | 0.0012 | 0.29 | 0.5285 |
| CKS1B | 20 | (15.5) | 39 | (57.4) | <0.0001 | 0.50 | 0.0002 |
| PB591 | 23 | (17.8) | 38 | (55.9) | <0.0001 | 0.43 | 0.0873 |
| LENEP | 31 | (24.0) | 18 | (26.5) | 0.8389 | 0.03 | 0.6507 |
| ZFP67 | 27 | (20.9) | 29 | (42.6) | 0.0023 | 0.34 | 0.8717 |
| FLJ32934 | 28 | (21.7) | 11 | (16.2) | 0.4606 | −0.02 | 0.6207 |
| ADAM15 | 23 | (17.8) | 29 | (42.6) | 0.0003 | 0.23 | 0.2808 |
| EFNA4 | 26 | (20.2) | 23 | (33.8) | 0.0528 | 0.21 | 0.3212 |

*The 0-100 scale CKS1B amplification index is a weighted sum of the proportions of clonal cells with 3 copies of CKS1B and >= 4 copies of CKS1B, defined by (.34 * % 3 copies + .66 * % >= 4 copies)/.66.
[†]For a test of the independence of amplification and 4th quartile membership (N = 197).
[‡]Correlation between each gene's expression and the 0-100 scale CKS1B amplification index
[a]Log rank test for association of Q4 membership and overall survival (N = 351, 64 deaths)

Furthermore, the association of CKS1B amplification with survival and event-free survival was validated in a cohort of 224 patients lacking microarray data. CKS1B amplification levels were inversely correlated with both event-free survival (P<0.0001) and overall survival (P<0.0001, FIG. 6C). These effects were also observed when all 421 patients were considered (event-free survival, p<0.0001; overall survival, P<0.0001, FIG. 6D).

Next, multivariate proportional hazards analyses were performed using the 369 patients with both CKS1B amplification data and all additional risk factor data (Table 4). The 3 genetic risk factors (CKS1B amplification, chromosome band 13q14 deletion, and metaphase karyotype abnormalities) all independently conferred both inferior event-free and overall survival, whereas hypo-albuminemia was the only one of three standard prognostic factors that retained adverse implications for both endpoints examined. Collectively, these 6 variables accounted for 46% and 33% of variability in survival and event-free survival, respectively, with the 3 standard, non-genetic parameters contributing only an additional 7.2% and 7.4%. CKS1B amplification was an independent predictor of outcome both as a 0-100 scale index and as a two-group category (Table 4A and B) after adjustment for the variables mentioned above and for the plasma cell labeling index.

Figure 7:
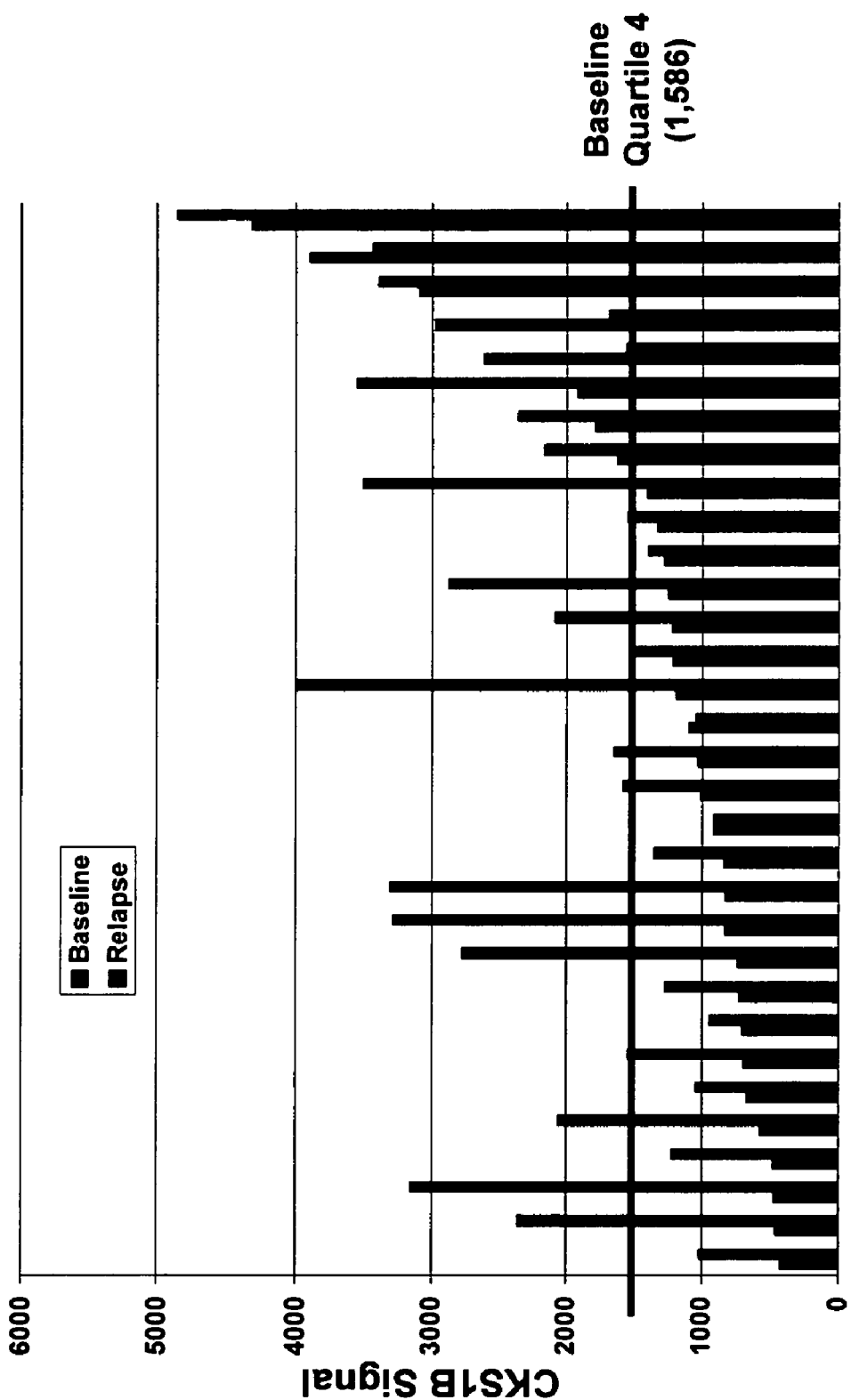
FIG. 7 shows that CKS1B expression increases in relapsed myeloma. CKS1B Signal for 32 paired diagnosis and relapse arrays. The quartile 4 reference line was taken from the complete (N=351) sample of arrays at diagnosis. Note that a majority of samples showed increased expression at relapse; the most dramatic changes were observed in patients with quartile 1-3 expression levels at diagnosis. A Welch-modified, paired t-test was used to compare log-scale Signal at diagnosis and relapse.

Paired CKS1B expression data at diagnosis and relapse, available in 32 cases, revealed increased expression in 84% at relapse (P=0.0001, FIG. 7), which was especially prominent in patients with quartile 1-3 expression levels at diagnosis. Paired CKS1B copy number data at diagnosis and relapse were available in 17 patients: of 7 lacking amplification at diagnosis, 4 demonstrated greater than equal to 3 copies at relapse; of 10 cases with 3 copies at diagnosis, 4 had acquired greater than equal to 4 copies at relapse; but 2 cases with 4 or more copies at diagnosis exhibited no further amplification at relapse.

Additionally, the relationship between CKS1B expression, CKS1B amplification and genetic subgroups was examined. The frequency of CKS1B quartile 4 expression varied among previously reported genetic subgroups (Fonseca et al., 2004) (Table 7A). With respect to gene expression-based translocations, nearly two-thirds of patients with MAF or MAFB activation, one-third each with FGFR3/MMSET and CCND1 activation, and only 18% without these translocations had CKS1B hyper-activation (P<0.0001). When examined in the context of metaphase karyotypes, CKS1B quartile 4 expression was present in approximately 20% of cases with hyperdiploid or normal, i.e. uninformative, karyotypes, whereas this feature was seen in nearly 50% of patients with hypodiploid and other cytogenetic abnormalities (P=0.0002).

In a separate multivariate analysis that was adjusted for genetic subgroups, CKS1B quartile 4 expression remained an independent adverse outcome predictor (Table 7B); the gene expression-derived translocation category as a whole conferred inferior event-free (P=0.034) but not overall survival (P=0.261); which was consistent with published data (Fonseca et al., 2004), CCND1 activation impacted both endpoints favorably. While not adjusted for the multiple log rank tests that identified the 70 genes, this analysis suggested that CKS1B expression retained explanatory power within relevant genetic subgroups.

TABLE 7A

Relationship between genetic abnormalities and CKS1B expression in quartile 4

| Abnormality Category[†] | n/347 (%) | CKS1B Q4 n | (%) | P-Value* |
|---|---|---|---|---|
| Expression-derived translocation | | | | |
| t(11; 14) | 60 (17.3) | 20 | (33.3) | <0.0001 |
| t(4; 14) | 48 (13.8) | 17 | (35.4) | |
| t(14; 16) & t(14; 20) | 14 (4.0) | 9 | (64.3) | |
| No Translocation Spike | 225 (64.8) | 41 | (18.2) | |
| Metaphase karyotype | | | | |
| Hyperdiploid | 55 (15.9) | 10 | (18.2) | 0.0002 |
| Non-hyperdiploid | 48 (13.8) | 24 | (50.0) | |
| Other Cytogenetics Abnormality | 9 (2.6) | 4 | (44.4) | |
| No Cytogenetics Abnormality | 235 (67.7) | 49 | (20.9) | |
| Chromosome 13 Deletion | n/334 | | | |
| No | 224 (67.1) | 47 | 21.0 | 0.02 |
| Yes | 110 (32.9) | 37 | 33.6 | |

[†]Translocations were determined from the expression spikes t(11; 14) = CCND1, t(4: 14) = FGFR3/MMSET, t(14; 16) = MAF and t(14; 20) = MAFB. Aneuploidy and other cytogenetic abnormalities were determined from cytogenetics, for which 4 observations were missing.
*Fisher's exact test of the independence of each category and CKS1B 4th quartile membership. Under the null hypothesis, Q4 contains on average 25% of patients within each level, corresponding to a proportional distribution across Q1-3 and Q4.

TABLE 7B

Multivariate analysis of CKS1B quartile 4 expression and cytogenetic abnormalities[†]

|  | Event-Free Survival | | Survival | |
|---|---|---|---|---|
|  | HR | P[‡] | HR | P[‡] |
| CKS1B Q4 | 1.97 | 0.003 | 2.16 | 0.005 |
| Expression-derived translocation* |  |  |  |  |
| t(11; 14) | 0.59 | 0.034 | 0.82 | 0.261 |
| t(4; 14) | 1.67 |  | 1.77 |  |
| t(14; 16) & t(14; 20) | 1.48 |  | 1.12 |  |
| Metaphase karyotype** |  |  |  |  |
| Hyperdiploid | 1.75 | 0.006 | 1.84 | 0.013 |
| Non-hyperdiploid | 2.29 |  | 2.56 |  |
| Other Cytogenetics Abnormality | 2.35 |  | 2.71 |  |
| r[2] | 0.218 |  | 0.223 |  |
| Events/Deaths | 97 |  | 63 |  |

[†]N = 347. Of 351 patients with expression data, 4 are missing cytogenetics.
[‡]Partial likelihood ratio test for the overall effect of the category.
*The P-value for modification of the CKS1B effect on EFS by translocation subgroup is 0.74.
**The P-value for modification of the CKS1B effect on EFS by karyotype subgroup is 0.27 and for survival it is 0.17. For survival, the hazard ratio for CKS1B is estimated to be 4.2 times higher in the non-hyperdiploid group compared to those with no abnormalities, with hazard ratios roughly the same for the other groups.

Figure 8A:
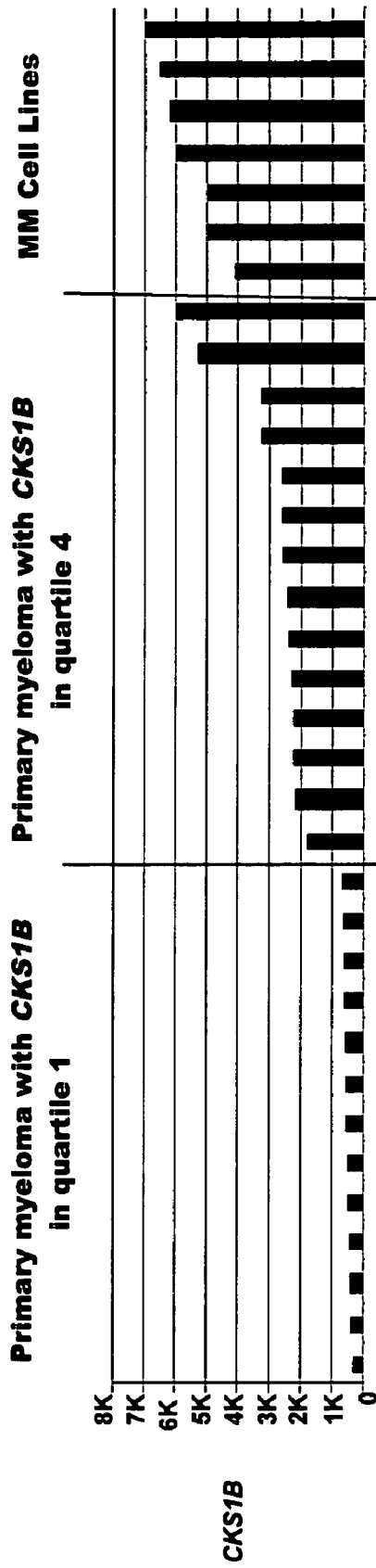
Figure 8B:
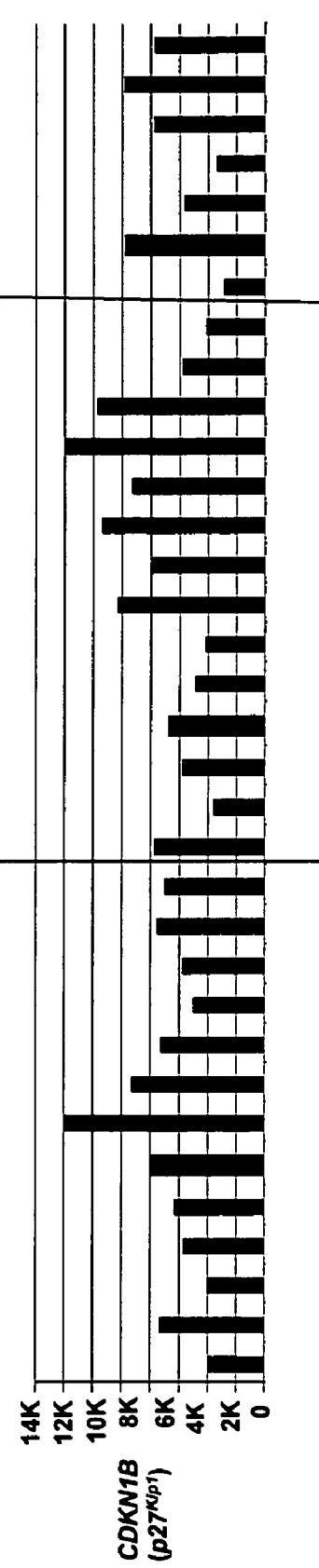

Furthermore, western blot analysis of nuclear protein from plasma cells from 27 newly diagnosed myeloma cases and 7 myeloma cell lines showed a strong correlation between CKS1B mRNA and protein, but no correlation between CDKN1B gene expression and CKS1B gene expression, protein levels or CDKN1B protein levels. However, CKS1B protein and CDKN1B protein levels showed an inverse correlation (FIG. 8). The cause for rare discrepancies (e.g. high CKS1B protein in the absence of elevated gene expression, was not clearly understood. Uniform histone 1A protein levels indicated equal protein loading across all samples. Cytoplasmic and non-phosphorylated-thr-187-CDKN1B levels were not altered in myeloma cell lysates with respect to CKS1B expression. Levels of CDKN1B protein were not correlated with the mRNA levels of SKP2.

Figures 8F, 8G:
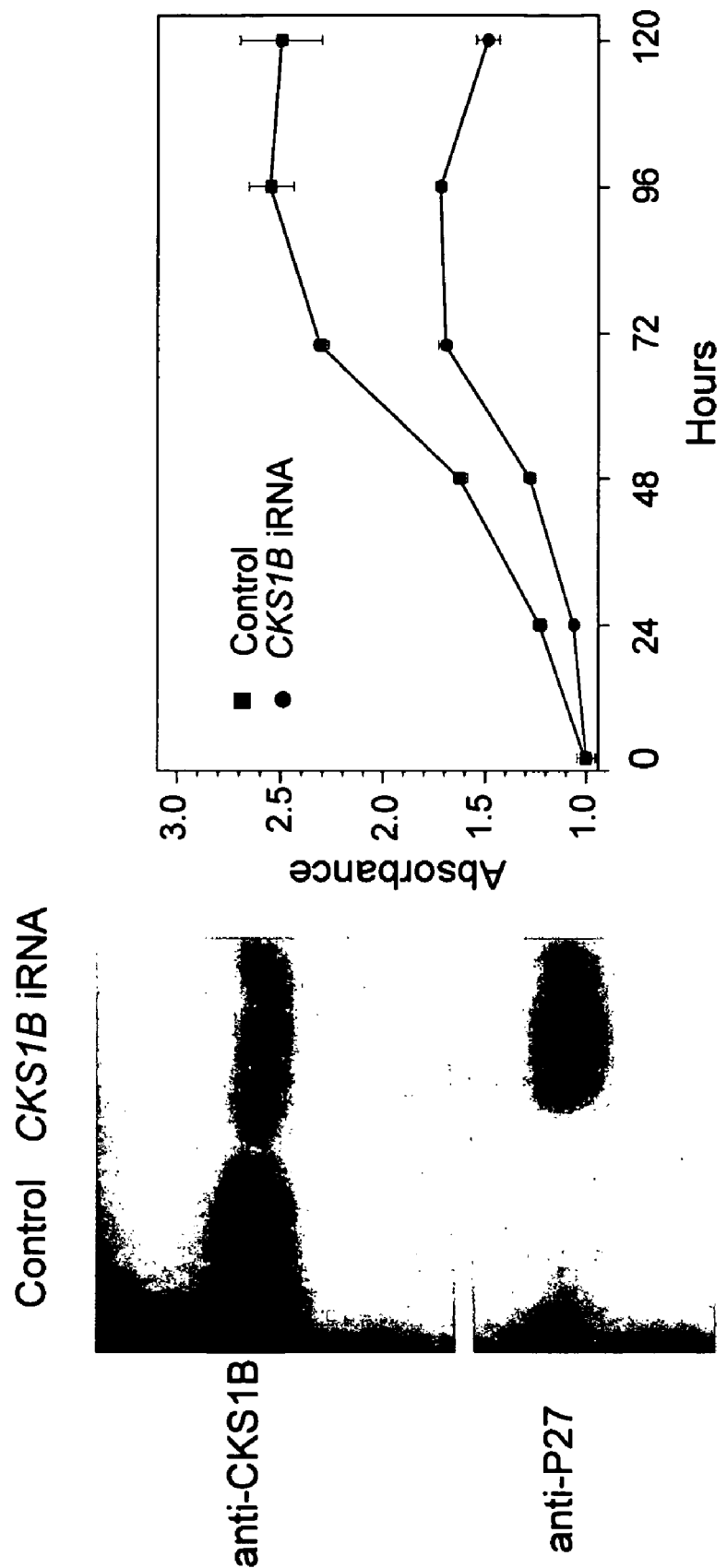
FIG. 8F shows Western blot analysis of I) CKS1B, II) phospho-thr-187-CDKN1B in ARP1 myeloma cells stably transfected with lentivirus expressing GFP and scrambled iRNA (left) and lentivirus expressing GFP and CKS1B iRNA (right).
FIG. 8G shows growth kinetics of the same cell line tested above. Error bars represent standard error of the mean for 6 replicates.

To confirm that CKS1B regulates CDKN1B and cell growth in myeloma, myeloma cell lines that constitutively express a small interfering RNA (siRNA) to CKS1B were created. 72 hours following infection of the ARP1 myeloma cell line, (containing 8 copies of CKS1B, the highest DNA copy number of 22 myeloma cell lines tested), with either lentivirus expressing siRNA to CKS1B or a scrambled siRNA, western blots analysis was performed (FIG. 8F). These experiments showed a reduction in CKS1B and increase in CDKN1B protein levels in CKS1B siRNA-positive cells relative to control cells. A time course analysis of ARP1 cell growth also revealed a reduction in cell proliferation in CKS1B siRNA-positive cells relative to controls (FIG. 8G). Similar results were observed with the OCI-My5, JJN3, and CAG myeloma cell lines.

Global gene expression analyses of highly purified plasma cells from newly diagnosed myeloma patients identified 70 genes that were significantly correlated with early disease-related mortality (median follow-up of 22 months). Importantly, 30% of these genes mapped to chromosome 1 suggesting an important role for this chromosome in myeloma disease progression. The increased expression of 1q genes and reduced expression of 1p genes were consistent with cytogenetic data of frequent 1q gains and 1p losses in myeloma karyotypes. (Nilsson et al., 2003; Gutierrez et al., 2004). Additionally, tandem duplications and jumping translocations involving 1q21, caused by decondensation of pericentromeric heterochromatin, are features of end stage disease (Sawyer et al., 2005; Sawyer et al., 1998).

Over-expression/amplification of CKS1B, mapping to 1q21, was linked to poor prognosis in early follow-up of newly diagnosed myeloma. The role of CKS1B in controlling $SCF^{Skp2}$-mediated ubiquitinylation and proteasomal degradation of the cyclin-dependent kinase inhibitor CDKN1B made it an attractive candidate gene. CKS1B protein levels were correlated with gene expression and were both inversely correlated with CDKN1B protein levels. Investigations in $S.$ $cerevisiae$ have demonstrated an essential role of cks1 in promoting mitosis by modulating the transcriptional activation of CDC20 (Morris et al., 2003). CKS1B and CDC20 expression were strongly correlated ($r=0.78$; $p<0.0001$), consistent with CKS1B promoting mitosis by regulating CDC20 expression in human cells. Thus, a gene dosage-related increase in CKS1B expression might lead to enhanced degradation of CDKN1B and also activation of CDC20 in myeloma.

In the context of recently recognized prognostically relevant genetic subgroups, CKS1B hyper-activation was less frequent in cases with hyperdiploid and normal karyotypes; one-third of those with CCND1-translocations had high CKS1B levels; and up to two-thirds of high-risk entities, MAF, MAFB and hypodiploidy displayed CKS1B hyperactivation (Table 7A). In addition to conferring a poor prognosis among newly diagnosed patients, CKS1B over-expression and amplification were common at relapse in patients lacking these features at diagnosis. Thus, it will be important to determine whether CKS1B amplification emerges in all subgroups and, when present, portends rapid disease progression and death. Moreover, since 1q21 amplification is frequent observation in many advanced solid and hematological malignancies, it will be important to determine if CKS1B gene amplification is associated with disease aggressiveness in a larger proportion of cancers.

Furthermore, CKS1B gene amplification along with chromosome 13q14 deletion and abnormal metaphase cytogenetics accounted for almost 40% of the observed survival variability, underscoring that myeloma risk is best assessed by molecular and cellular genetic tests. Routine application of such studies, performed on a single bone marrow sample, is therefore recommended for appropriate patient stratification in therapeutic trial design. Additionally, the survival impact of new agents, such as bortezomib and thalidomide and its derivatives, will be profound if their clinical efficacy also extends to genetically defined high-risk myeloma, which has not been investigated. Since CKS1B appears to directly or indirectly interact with ubiquitin ligases and/or the proteasome to regulate multiple cell cycle checkpoints (Pagano and Benmaamar, 2003), new therapeutic strategies that directly target CKS1B or related pathways may represent novel, and more specific, means of treating de novo high-risk myeloma and may prevent its secondary evolution.

Given the negative impact of chromosome band 13q14 deletion on survival, it is noteworthy that reduced expression of a single gene mapping to chromosome 13q14, RFP2/LEU5, which was previously identified as a candidate tumor suppressor gene with significant homology to BRCA1 (Kapandaze et al., 1998), was significantly linked to poor survival in this analysis, and suggests that an in-depth investigation of RFP2 function and mutation analysis in myeloma is warranted.

Additionally, cyclin D dysregulation is a common event in cancer and contributes to tumorigenesis by promoting hyperphosphorylation of the RB1 protein and activation of E2F target genes important in promoting transition through early G1 to S checkpoint of the cell cycle. Previous study had reported that dysregulated expression of one of the three D-type cyclins was likely to be a unifying initiating genetic lesion in multiple myeloma. Based on the available information and the results presented herein, a multistep pathogenic model of myelomagensis is contemplated in which activation of a D type cyclin is an early initiating event and CKS1B amplification is a progression event, resulting in loss of both early amd late G1 to S checkpoints of the cell cycle and establishment of an aggressive, multidrug resistant disease.

The following references are cited herein:

Abraham R. S. et al., *Blood*, 2005, 105:794-803.
Attal M. et al., *N Engl J Med*, 2003, 349:2495-502.
Barlogie B. et al., *Williams Hematology*, 2001, 1279-1304.
Barlogie B. et al. *Blood*, 2004, 103:20-32.
Bullinger L. et al., *N Engl J Med*, 2004, 350:1605-16.
Claudio J. O. et al., *Blood*, 2002, 100:21714d
De Vos J. et al., *Oncogene*, 2002, 21:6848-57.
DeWald G. W. et al., *Blood*, 1985, 66:380-390.
Fonseca R. et al. *Cancer Res*, 2004, 64:1546-58.
Ganoth D. et al., *Nat Cell Biol*, 2001, 3:321-4
Gutierrez, N. C. et al., *Blood*, 2004, 104:2661-6.
Hideshima T. et al., *Blood* 2004, 104:607-18.
Kapanadze, B. et al., *FEBS Lett*. 1998, 426: 266-270.
Kitajima, S. et al., *Am J Pathol*, 2004, 165: 2147-2155.
Kuehl W. M. and Bergsagel P. L., *Nature Rev Cancer* 2002, 2:175-187.
Le Baccon, P. Genes *Chromosomes Cancer*, 2001, 32:250-64.
McCoy J. et al. *Blood*, 2003,102:2512a.
Morris M. C. et al., *Nature*, 2003, 423(6943):1009-13.
Nakayama K. et al., *Dev Cell*, 2004, 6:661-72.
Nilsson T. et al. *Br J Haematol.*, 2003, 120:960-9.
O'Quigley J. and Xu R. Explained variation in proportional hazards regression. In: Crowley J, ed. Handbook of Statistics in Clinical Oncology. New York, N.Y.: Marcel Dekker, 2001:397-410.
Pagano M., *Mol Cell*, 2004,14:414-6.
Pagano, M. and Benmaamar, R. *Cancer Cell*, 2003, 4:251-6.
Peters J. M. *Mol. Cell*, 2002, 95:931-43.
Philip P. et al., *Cancer Genetics and Cytogenetics*, 1980, 2:243-257.
R Development Core Team. R: A language and environment for statistical computing. R Foundation for Statistical Computing, Vienna, Austria. 2004. ISBN 3-900051-07-0, www.R-project.org.
Rosenwald A., et al., *N Engl J Med*, 2002, 346:1937-47.
Sawyer J. R. et al. *Genes Chromosomes Cancer*, 2005, 42:95-106.
Sawyer, J. R. et al, *Blood*, 1998, 91:1732-41.
Smadja N. V. et al., *Blood*, 2001; 98:2229-2238.
Shaughnessy J. and Barlogie B. *Immunol Rev*, 2003, 94:140-63.
Shaughnessy J. et al., *Blood*, 2003, 101:3849-3856.
Shaughnessy J Jr. et al., *Br J Haematol.* 2003, 120:44-52.
Shaughnessy J. et al., *Blood* 2000, 96:1505-11.
Sherr C. J. et al., *Genes Dev.;* 1999, 13:1501-12.
Shipp M. A. et al., *Nat Med*, 2002, 8:68-74.
Slingerland J. and Pagano M., *J Cell Physiol*, 2000, 183:10-17.
Spruck C. et al., *Mol Cell*, 2001, 7:639-50.
Storey and Tibshirani, *Proc Natl Acad. Sci.* 2003, 100(16): 9440-9445.
Tian E. et al., *N Eng J Med* 2003, 349:2483-94.
Valk P. J et al., *N Engl J Med*, 2004, 350:1617-28.
Yeoh E, J. et al., *Cancer Cell*, 2002, 1:133-143.
Zhan, F. et al., *Blood*, 2002, 99:1745-57.
Zufferey, R. et al., *Nat Biotechnol*, 1997, 15: 871-875.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

What is claimed is:

1. A method of determining the prognosis of a multiple myeloma patient, comprising the steps of:
   obtaining plasma cells from said patient; and
   determining copy number of CKS1B gene in the plasma cell, wherein increased copy number of said gene compared to copy number of the same gene in a plasma cell of a control individual indicates that said patient would have a poor prognosis indicating high risk of relapse in said patient after treatment.

2. The method of claim 1, wherein said treatment is high dose chemotherapy and autologous peripheral blood stem cell transplantation.

3. The method of claim 1, wherein said control individual is a normal healthy individual or an individual diagnosed with multiple myeloma lacking decreased copy number, increased copy number or a combination thereof of the gene.

4. The method of claim 1, wherein the copy number of the gene is determined by fluorescence in situ hybridization.

* * * * *